(12) United States Patent
Goraltchouk et al.

(10) Patent No.: US 8,876,865 B2
(45) Date of Patent: Nov. 4, 2014

(54) SELF-RETAINING SUTURES WITH BI-DIRECTIONAL RETAINERS OR UNI-DIRECTIONAL RETAINERS

(75) Inventors: Alexei Goraltchouk, Goleta, CA (US); Lev Drubetsky, Coquitlam (CA); Gerald F. Cummings, Port Moody (CA); Robert A. Herrmann, Vancouver (CA); Alexander Naimagon, Richmond (CA)

(73) Assignee: Ethicon, Inc., Somerville, NJ (US)

( * ) Notice: Subject to any disclaimer, the term of this patent is extended or adjusted under 35 U.S.C. 154(b) by 626 days.

(21) Appl. No.: 12/937,776

(22) PCT Filed: Apr. 14, 2009

(86) PCT No.: PCT/US2009/040545
§ 371 (c)(1),
(2), (4) Date: Mar. 1, 2011

(87) PCT Pub. No.: WO2009/129251
PCT Pub. Date: Oct. 22, 2009

(65) Prior Publication Data
US 2011/0288583 A1    Nov. 24, 2011

Related U.S. Application Data

(60) Provisional application No. 61/045,075, filed on Apr. 15, 2008.

(51) Int. Cl.
*A61B 17/04* (2006.01)
*A61B 17/06* (2006.01)
*A61B 17/08* (2006.01)
*A61B 17/00* (2006.01)

(52) U.S. Cl.
CPC . *A61B 17/06166* (2013.01); *A61B 2017/06176* (2013.01); *A61B 2017/081* (2013.01); *A61B 2017/00526* (2013.01); *A61B 17/08* (2013.01)
USPC .......................................... 606/228; 606/232

(58) Field of Classification Search
USPC .................................................. 606/228–231
See application file for complete search history.

(56) References Cited

U.S. PATENT DOCUMENTS

| 709,392 A | 9/1902 | Brown |
| 733,723 A | 7/1903 | Lukens |

(Continued)

FOREIGN PATENT DOCUMENTS

| BE | 1014364 | 9/2003 |
| CA | 2309844 | 12/1996 |

(Continued)

OTHER PUBLICATIONS

US 6,447,535, (withdrawn).

(Continued)

*Primary Examiner* — Melanie Tyson
*Assistant Examiner* — Todd J Scherbel

(57) ABSTRACT

Provided herein are sutures for use in a procedure applied to tissue, and methods for forming such sutures. Some sutures include bi-directional retainers, each of which can be deployed in two directions, but once deployed in one direction, resist motion in the opposite direction. Other sutures include uni-directional retainers that are conical in shape, and include tissue engaging protrusions that extend from edges and/or angled walls of the conical retainers.

9 Claims, 6 Drawing Sheets

(56) References Cited

U.S. PATENT DOCUMENTS

| | | |
|---|---|---|
| 789,401 A | 5/1905 | Acheson |
| 816,026 A | 3/1906 | Meier |
| 879,758 A | 2/1908 | Foster |
| 1,142,510 A | 6/1915 | Engle |
| 1,248,825 A | 12/1917 | Dederer |
| 1,321,011 A | 11/1919 | Cottes |
| 1,558,037 A | 10/1925 | Morton |
| 1,728,316 A | 9/1929 | Von Wachenfeldt |
| 1,886,721 A | 11/1932 | O'Brien |
| 2,094,578 A | 10/1937 | Blumenthal et al. |
| 2,201,610 A | 5/1940 | Dawson, Jr. |
| 2,232,142 A | 2/1941 | Schumann |
| 2,254,620 A | 9/1941 | Miller |
| 2,347,956 A | 5/1944 | Lansing |
| 2,355,907 A | 8/1944 | Cox |
| 2,421,193 A | 5/1947 | Gardner |
| 2,452,734 A | 11/1948 | Costelow |
| 2,472,009 A | 5/1949 | Gardner |
| 2,480,271 A | 8/1949 | Sumner |
| 2,572,936 A | 10/1951 | Kulp et al. |
| 2,684,070 A | 7/1954 | Kelsey |
| 2,736,964 A | 3/1956 | Lieberman |
| 2,779,083 A | 1/1957 | Enton |
| 2,814,296 A | 11/1957 | Everett |
| 2,817,339 A | 12/1957 | Sullivan |
| 2,866,256 A | 12/1958 | Matlin |
| 2,910,067 A | 10/1959 | White |
| 2,928,395 A | 3/1960 | Forbes et al. |
| 2,988,028 A | 6/1961 | Alcamo |
| 3,003,155 A | 10/1961 | Mielzynski et al. |
| 3,066,452 A | 12/1962 | Bott et al. |
| 3,066,673 A | 12/1962 | Bott et al. |
| 3,068,869 A | 12/1962 | Shelden et al. |
| 3,068,870 A | 12/1962 | Levin |
| 3,123,077 A * | 3/1964 | Alcoma ................ 606/228 |
| 3,166,072 A | 1/1965 | Sullivan, Jr. |
| 3,187,752 A | 6/1965 | Glick |
| 3,206,018 A | 9/1965 | Lewis et al. |
| 3,209,652 A | 10/1965 | Burgsmueller |
| 3,209,754 A | 10/1965 | Brown |
| 3,212,187 A | 10/1965 | Benedict |
| 3,214,810 A | 11/1965 | Mathison |
| 3,221,746 A | 12/1965 | Noble |
| 3,234,636 A | 2/1966 | Brown |
| 3,273,562 A | 9/1966 | Brown |
| 3,352,191 A | 11/1967 | Crawford |
| 3,378,010 A | 4/1968 | Codling |
| 3,385,299 A | 5/1968 | LeRoy |
| 3,394,704 A | 7/1968 | Dery |
| 3,494,006 A | 2/1970 | Brumlik |
| 3,522,637 A | 8/1970 | Brumlik |
| 3,525,340 A | 8/1970 | Gilbert |
| 3,527,223 A | 9/1970 | Shein |
| 3,545,608 A | 12/1970 | Berger et al. |
| 3,557,795 A | 1/1971 | Hirsch |
| 3,570,497 A | 3/1971 | Lemole |
| 3,586,002 A | 6/1971 | Wood |
| 3,608,095 A | 9/1971 | Barry |
| 3,608,539 A | 9/1971 | Miller |
| 3,618,447 A | 11/1971 | Goins |
| 3,646,615 A | 3/1972 | Ness |
| 3,683,926 A | 8/1972 | Suzuki |
| 3,700,433 A | 10/1972 | Duhl |
| 3,716,058 A | 2/1973 | Tanner, Jr. |
| 3,720,055 A | 3/1973 | de Mestral et al. |
| 3,748,701 A | 7/1973 | De Mestral |
| 3,762,418 A | 10/1973 | Wasson |
| 3,825,010 A | 7/1974 | McDonald |
| 3,833,972 A | 9/1974 | Brumlik |
| 3,845,641 A | 11/1974 | Waller |
| 3,847,156 A | 11/1974 | Trumble |
| 3,889,322 A | 6/1975 | Brumlik |
| 3,918,455 A | 11/1975 | Coplan |
| 3,922,455 A | 11/1975 | Brumlik |
| 3,941,164 A | 3/1976 | Musgrave |
| 3,951,261 A | 4/1976 | Mandel et al. |
| 3,963,031 A | 6/1976 | Hunter |
| 3,980,177 A | 9/1976 | McGregor |
| 3,981,051 A | 9/1976 | Brumlik |
| 3,981,307 A | 9/1976 | Borysko |
| 3,985,138 A | 10/1976 | Jarvik |
| 3,985,227 A | 10/1976 | Thyen et al. |
| 3,990,144 A | 11/1976 | Schwartz |
| 4,006,747 A | 2/1977 | Kronenthal |
| 4,008,303 A | 2/1977 | Glick et al. |
| 4,027,608 A | 6/1977 | Arbuckle |
| 4,043,344 A | 8/1977 | Landi |
| 4,052,988 A | 10/1977 | Doddi et al. |
| D246,911 S | 1/1978 | Bess, Jr. et al. |
| 4,069,825 A | 1/1978 | Akiyama |
| 4,073,298 A | 2/1978 | Le Roy |
| 4,137,921 A | 2/1979 | Okuzumi et al. |
| 4,182,340 A | 1/1980 | Spencer |
| 4,186,239 A | 1/1980 | Mize et al. |
| 4,198,734 A | 4/1980 | Brumlik |
| 4,204,541 A | 5/1980 | Kapitanov |
| 4,204,542 A | 5/1980 | Bokros et al. |
| 4,259,959 A | 4/1981 | Walker |
| 4,278,374 A | 7/1981 | Wolosianski |
| 4,300,424 A | 11/1981 | Flinn |
| 4,311,002 A | 1/1982 | Hoffmann et al. |
| 4,313,448 A | 2/1982 | Stokes |
| 4,316,469 A | 2/1982 | Kapitanov |
| 4,317,451 A | 3/1982 | Cerwin et al. |
| 4,372,293 A | 2/1983 | Vijil-Rosales |
| 4,428,376 A | 1/1984 | Mericle |
| 4,430,998 A | 2/1984 | Harvey |
| 4,434,796 A | 3/1984 | Karapetian |
| 4,449,298 A | 5/1984 | Patz |
| 4,454,875 A | 6/1984 | Pratt et al. |
| 4,467,805 A | 8/1984 | Fukuda |
| 4,490,326 A | 12/1984 | Beroff et al. |
| 4,492,075 A | 1/1985 | Faure |
| 4,493,323 A | 1/1985 | Albright et al. |
| 4,505,274 A | 3/1985 | Speelman |
| 4,510,934 A | 4/1985 | Batra |
| 4,531,522 A | 7/1985 | Bedi et al. |
| 4,532,926 A | 8/1985 | O'Holla |
| 4,535,772 A | 8/1985 | Sheehan |
| 4,548,202 A | 10/1985 | Duncan |
| 4,553,544 A | 11/1985 | Nomoto et al. |
| 4,610,250 A | 9/1986 | Green |
| 4,610,251 A | 9/1986 | Kumar |
| 4,635,637 A | 1/1987 | Schreiber |
| 4,637,380 A | 1/1987 | Orejola |
| 4,653,486 A | 3/1987 | Coker |
| 4,669,473 A | 6/1987 | Richards et al. |
| 4,676,245 A | 6/1987 | Fukuda |
| 4,689,882 A | 9/1987 | Lorenz |
| 4,702,250 A | 10/1987 | Ovil et al. |
| 4,719,917 A | 1/1988 | Barrows |
| 4,741,330 A | 5/1988 | Hayhurst |
| 4,750,910 A | 6/1988 | Takayanagi et al. |
| 4,751,621 A | 6/1988 | Jenkins |
| 4,776,337 A | 10/1988 | Palmaz |
| 4,832,025 A | 5/1989 | Coates |
| 4,841,960 A | 6/1989 | Garner |
| 4,865,026 A | 9/1989 | Barrett |
| 4,873,976 A | 10/1989 | Schreiber |
| 4,887,601 A | 12/1989 | Richards |
| 4,895,148 A | 1/1990 | Bays et al. |
| 4,898,156 A | 2/1990 | Gatturna et al. |
| 4,899,743 A | 2/1990 | Nicholson et al. |
| 4,900,605 A | 2/1990 | Thorgersen et al. |
| 4,905,367 A | 3/1990 | Pinchuck et al. |
| 4,930,945 A | 6/1990 | Arai et al. |
| 4,932,962 A | 6/1990 | Yoon et al. |
| 4,946,468 A | 8/1990 | Li |
| 4,948,444 A | 8/1990 | Schultz et al. |
| 4,950,258 A | 8/1990 | Kawai et al. |
| 4,950,285 A | 8/1990 | Wilk |
| 4,968,315 A | 11/1990 | Gatturna |
| 4,976,715 A | 12/1990 | Bays et al. |
| 4,979,956 A | 12/1990 | Silvestrini et al. |

(56) References Cited

U.S. PATENT DOCUMENTS

| | | |
|---|---|---|
| 4,981,149 A | 1/1991 | Yoon |
| 4,994,073 A | 2/1991 | Green |
| 4,994,084 A | 2/1991 | Brennan |
| 4,997,439 A | 3/1991 | Chen |
| 5,002,550 A | 3/1991 | Li |
| 5,002,562 A | 3/1991 | Oberlander |
| 5,007,921 A | 4/1991 | Brown |
| 5,007,922 A | 4/1991 | Chen et al. |
| 5,026,390 A | 6/1991 | Brown |
| 5,037,422 A | 8/1991 | Hayhurst et al. |
| 5,037,433 A | 8/1991 | Wilk et al. |
| 5,041,129 A | 8/1991 | Hayhurst et al. |
| 5,046,513 A | 9/1991 | Gatturna et al. |
| 5,047,047 A | 9/1991 | Yoon |
| 5,053,047 A | 10/1991 | Yoon |
| 5,084,063 A | 1/1992 | Korthoff |
| 5,089,010 A | 2/1992 | Korthoff |
| 5,101,968 A | 4/1992 | Henderson et al. |
| 5,102,418 A | 4/1992 | Granger et al. |
| 5,102,421 A | 4/1992 | Anpach, Jr. |
| 5,103,073 A | 4/1992 | Danilov et al. |
| 5,112,344 A | 5/1992 | Petros |
| 5,123,911 A | 6/1992 | Granger et al. |
| 5,123,913 A * | 6/1992 | Wilk et al. ............... 606/232 |
| 5,123,919 A | 6/1992 | Sauter et al. |
| 5,127,413 A | 7/1992 | Ebert |
| 5,133,738 A | 7/1992 | Korthoff et al. |
| 5,141,520 A | 8/1992 | Goble et al. |
| 5,147,382 A | 9/1992 | Gertzman et al. |
| 5,156,615 A | 10/1992 | Korthoff et al. |
| 5,156,788 A | 10/1992 | Chesterfield et al. |
| 5,176,692 A | 1/1993 | Wilk et al. |
| 5,179,964 A | 1/1993 | Cook |
| 5,192,274 A | 3/1993 | Bierman |
| 5,192,302 A | 3/1993 | Kensey et al. |
| 5,192,303 A | 3/1993 | Gatturna et al. |
| 5,197,597 A | 3/1993 | Leary et al. |
| 5,201,326 A | 4/1993 | Kubicki et al. |
| 5,207,679 A | 5/1993 | Li |
| 5,207,694 A | 5/1993 | Broome |
| 5,217,486 A | 6/1993 | Rice et al. |
| 5,217,494 A | 6/1993 | Coggins et al. |
| 5,222,508 A | 6/1993 | Contarini |
| 5,222,976 A | 6/1993 | Yoon |
| 5,224,946 A | 7/1993 | Hayhurst et al. |
| 5,234,006 A | 8/1993 | Eaton et al. |
| 5,242,457 A | 9/1993 | Akopov et al. |
| 5,246,441 A | 9/1993 | Ross et al. |
| 5,249,673 A | 10/1993 | Sinn |
| 5,258,013 A | 11/1993 | Granger et al. |
| 5,259,846 A | 11/1993 | Granger et al. |
| 5,263,973 A | 11/1993 | Cook |
| 5,269,783 A | 12/1993 | Sander |
| 5,282,832 A | 2/1994 | Toso et al. |
| 5,292,326 A | 3/1994 | Green |
| 5,306,288 A | 4/1994 | Granger et al. |
| 5,306,290 A | 4/1994 | Martins et al. |
| 5,312,422 A | 5/1994 | Trott |
| 5,320,629 A | 6/1994 | Noda et al. |
| 5,330,488 A | 7/1994 | Goldrath |
| 5,330,503 A * | 7/1994 | Yoon ............... 606/223 |
| 5,336,239 A | 8/1994 | Gimpelson |
| 5,341,922 A | 8/1994 | Cerwin et al. |
| 5,342,376 A | 8/1994 | Ruff |
| 5,342,395 A | 8/1994 | Jarrett et al. |
| 5,350,385 A | 9/1994 | Christy |
| 5,352,515 A | 10/1994 | Jarrett et al. |
| 5,354,271 A | 10/1994 | Voda |
| 5,354,298 A | 10/1994 | Lee et al. |
| 5,358,511 A | 10/1994 | Gatturna et al. |
| 5,363,556 A | 11/1994 | Banholzer et al. |
| 5,372,146 A | 12/1994 | Branch |
| 5,374,268 A | 12/1994 | Sander |
| 5,374,278 A | 12/1994 | Chesterfield et al. |
| 5,380,334 A | 1/1995 | Torrie et al. |
| 5,391,173 A | 2/1995 | Wilk |
| 5,395,126 A | 3/1995 | Tresslar |
| 5,403,346 A | 4/1995 | Loeser |
| 5,411,523 A | 5/1995 | Goble |
| 5,414,988 A | 5/1995 | DiPalma et al. |
| 5,417,691 A | 5/1995 | Hayhurst |
| 5,425,746 A | 6/1995 | Proto et al. |
| 5,425,747 A | 6/1995 | Brotz |
| 5,437,680 A | 8/1995 | Yoon et al. |
| 5,450,860 A | 9/1995 | O'Connor |
| 5,451,461 A | 9/1995 | Broyer |
| 5,462,561 A | 10/1995 | Voda |
| 5,464,422 A | 11/1995 | Silverman |
| 5,464,426 A | 11/1995 | Bonutti |
| 5,464,427 A | 11/1995 | Curtis et al. |
| 5,472,452 A | 12/1995 | Trott |
| 5,478,353 A | 12/1995 | Yoon |
| 5,480,403 A | 1/1996 | Lee et al. |
| 5,480,411 A | 1/1996 | Liu et al. |
| 5,484,451 A | 1/1996 | Akopov et al. |
| 5,486,197 A | 1/1996 | Le et al. |
| 5,494,154 A | 2/1996 | Ainsworth et al. |
| 5,500,000 A | 3/1996 | Feagin et al. |
| 5,500,991 A | 3/1996 | Demarest et al. |
| 5,520,084 A | 5/1996 | Chesterfield et al. |
| 5,520,691 A | 5/1996 | Branch |
| 5,522,845 A | 6/1996 | Wenstrom, Jr. |
| 5,527,342 A | 6/1996 | Pietrzak et al. |
| 5,531,760 A | 7/1996 | Alwafaie |
| 5,531,761 A | 7/1996 | Yoon |
| 5,531,790 A | 7/1996 | Frechet et al. |
| 5,533,982 A | 7/1996 | Rizk et al. |
| 5,536,582 A | 7/1996 | Prasad et al. |
| 5,540,705 A | 7/1996 | Meade et al. |
| 5,540,718 A | 7/1996 | Bartlett |
| 5,545,148 A | 8/1996 | Wurster |
| 5,546,957 A | 8/1996 | Heske |
| 5,549,631 A | 8/1996 | Bonutti |
| 5,554,171 A | 9/1996 | Gatturna et al. |
| 5,566,822 A | 10/1996 | Scanlon |
| 5,569,272 A | 10/1996 | Reed et al. |
| 5,571,139 A | 11/1996 | Jenkins, Jr. |
| 5,571,175 A | 11/1996 | Vanney et al. |
| 5,571,216 A | 11/1996 | Anderson |
| 5,573,543 A | 11/1996 | Akopov et al. |
| 5,584,859 A | 12/1996 | Brotz |
| 5,601,557 A | 2/1997 | Hayhurst |
| 5,626,590 A | 5/1997 | Wilk |
| 5,626,611 A | 5/1997 | Liu et al. |
| 5,632,753 A | 5/1997 | Loeser |
| 5,643,288 A | 7/1997 | Thompson |
| 5,643,295 A | 7/1997 | Yoon |
| 5,643,319 A | 7/1997 | Green et al. |
| 5,645,568 A | 7/1997 | Chervitz et al. |
| 5,647,874 A | 7/1997 | Hayhurst |
| 5,649,939 A | 7/1997 | Reddick |
| 5,653,716 A | 8/1997 | Malo et al. |
| 5,662,714 A | 9/1997 | Charvin et al. |
| 5,669,935 A | 9/1997 | Rosenman et al. |
| 5,676,675 A | 10/1997 | Grice |
| D386,583 S | 11/1997 | Ferragamo et al. |
| 5,683,417 A | 11/1997 | Cooper |
| D387,161 S | 12/1997 | Ferragamo et al. |
| 5,693,072 A | 12/1997 | McIntosh |
| 5,695,879 A | 12/1997 | Goldmann et al. |
| 5,697,976 A | 12/1997 | Chesterfield et al. |
| 5,702,397 A | 12/1997 | Goble et al. |
| 5,702,462 A | 12/1997 | Oberlander |
| 5,709,692 A | 1/1998 | Mollenauer et al. |
| 5,716,358 A | 2/1998 | Ochoa et al. |
| 5,716,376 A | 2/1998 | Roby et al. |
| 5,722,991 A | 3/1998 | Colligan |
| 5,723,008 A | 3/1998 | Gordon |
| 5,725,557 A | 3/1998 | Gatturna et al. |
| 5,728,114 A | 3/1998 | Evans et al. |
| 5,731,855 A | 3/1998 | Koyama et al. |
| 5,741,277 A | 4/1998 | Gordon et al. |
| 5,744,151 A | 4/1998 | Capelli |
| 5,763,411 A | 6/1998 | Edwardson et al. |

(56) References Cited

U.S. PATENT DOCUMENTS

| | | |
|---|---|---|
| 5,765,560 A | 6/1998 | Verkerke et al. |
| 5,766,246 A | 6/1998 | Mulhauser et al. |
| 5,779,719 A | 7/1998 | Klein et al. |
| 5,782,864 A | 7/1998 | Lizardi |
| 5,807,403 A | 9/1998 | Beyar et al. |
| 5,807,406 A | 9/1998 | Brauker et al. |
| 5,810,853 A | 9/1998 | Yoon |
| 5,814,051 A | 9/1998 | Wenstrom, Jr. |
| 5,843,087 A | 12/1998 | Jensen et al. |
| 5,843,178 A | 12/1998 | Vanney et al. |
| 5,855,619 A | 1/1999 | Caplan et al. |
| 5,863,360 A | 1/1999 | Wood et al. |
| 5,884,859 A | 3/1999 | Ma |
| 5,887,594 A | 3/1999 | LoCicero, III |
| 5,891,166 A | 4/1999 | Schervinsky |
| 5,893,856 A | 4/1999 | Jacob et al. |
| 5,895,395 A | 4/1999 | Yeung |
| 5,895,413 A | 4/1999 | Nordstrom |
| 5,897,572 A | 4/1999 | Schulsinger et al. |
| 5,899,911 A | 5/1999 | Carter |
| 5,916,224 A | 6/1999 | Esplin |
| 5,919,234 A | 7/1999 | Lemperle et al. |
| 5,921,982 A | 7/1999 | Lesh et al. |
| 5,925,078 A | 7/1999 | Anderson |
| 5,931,855 A | 8/1999 | Buncke |
| 5,935,138 A | 8/1999 | McJames, II et al. |
| 5,938,668 A | 8/1999 | Scirica et al. |
| 5,941,899 A | 8/1999 | Granger et al. |
| 5,950,633 A | 9/1999 | Lynch et al. |
| 5,954,747 A | 9/1999 | Clark |
| 5,964,765 A | 10/1999 | Fenton, Jr. et al. |
| 5,964,783 A | 10/1999 | Grafton et al. |
| 5,968,097 A | 10/1999 | Frechet et al. |
| 5,972,024 A | 10/1999 | Northrup, III et al. |
| 5,984,933 A | 11/1999 | Yoon |
| 5,993,459 A | 11/1999 | Larsen et al. |
| 6,001,111 A | 12/1999 | Sepetka et al. |
| 6,012,216 A | 1/2000 | Esteves et al. |
| 6,015,410 A | 1/2000 | Tormala et al. |
| 6,024,757 A | 2/2000 | Haase et al. |
| 6,027,523 A | 2/2000 | Schmieding |
| 6,039,741 A | 3/2000 | Meislin |
| 6,056,778 A | 5/2000 | Grafton et al. |
| 6,063,105 A | 5/2000 | Totakura |
| 6,071,292 A | 6/2000 | Makower et al. |
| 6,074,419 A | 6/2000 | Healy et al. |
| 6,076,255 A | 6/2000 | Shikakubo et al. |
| 6,083,244 A | 7/2000 | Lubbers et al. |
| 6,102,947 A | 8/2000 | Gordon |
| 6,106,544 A | 8/2000 | Brazeau |
| 6,106,545 A | 8/2000 | Egan |
| 6,110,484 A | 8/2000 | Sierra |
| 6,129,741 A | 10/2000 | Wurster et al. |
| D433,753 S | 11/2000 | Weiss |
| 6,146,406 A | 11/2000 | Shluzas et al. |
| 6,146,407 A | 11/2000 | Krebs |
| 6,149,660 A | 11/2000 | Laufer et al. |
| 6,163,948 A | 12/2000 | Esteves et al. |
| 6,165,203 A | 12/2000 | Krebs |
| 6,168,633 B1 | 1/2001 | Shoher et al. |
| 6,174,324 B1 | 1/2001 | Egan et al. |
| 6,183,499 B1 | 2/2001 | Fischer et al. |
| 6,187,095 B1 | 2/2001 | Labrecque et al. |
| 6,203,565 B1 | 3/2001 | Bonutti et al. |
| 6,206,908 B1 | 3/2001 | Roby |
| 6,214,030 B1 | 4/2001 | Matsutani et al. |
| 6,231,911 B1 | 5/2001 | Steinback et al. |
| 6,235,869 B1 | 5/2001 | Roby et al. |
| 6,241,747 B1 | 6/2001 | Ruff |
| 6,251,143 B1 | 6/2001 | Schwartz et al. |
| 6,264,675 B1 | 7/2001 | Brotz |
| 6,267,772 B1 | 7/2001 | Mulhauser et al. |
| 6,270,517 B1 | 8/2001 | Brotz |
| 6,315,788 B1 | 11/2001 | Roby |
| 6,319,231 B1 | 11/2001 | Andrulitis |
| 6,322,581 B1 | 11/2001 | Fukuda et al. |
| 6,334,865 B1 | 1/2002 | Redmond et al. |
| 6,383,201 B1 | 5/2002 | Dong |
| 6,387,363 B1 | 5/2002 | Gruskin |
| 6,388,043 B1 | 5/2002 | Langer et al. |
| 6,395,029 B1 | 5/2002 | Levy |
| D462,766 S | 9/2002 | Jacobs et al. |
| 6,443,962 B1 | 9/2002 | Gaber |
| 6,463,719 B2 | 10/2002 | Dey et al. |
| 6,471,715 B1 | 10/2002 | Weiss |
| 6,478,809 B1 | 11/2002 | Brotz |
| 6,485,503 B2 | 11/2002 | Jacobs et al. |
| 6,491,701 B2 | 12/2002 | Tierney et al. |
| 6,491,714 B1 | 12/2002 | Bennett |
| 6,494,898 B1 | 12/2002 | Roby et al. |
| 6,495,127 B1 | 12/2002 | Wallace et al. |
| RE37,963 E | 1/2003 | Thal |
| 6,506,190 B1 * | 1/2003 | Walshe ............... 606/139 |
| 6,506,197 B1 | 1/2003 | Rollero et al. |
| 6,511,488 B1 | 1/2003 | Marshall et al. |
| 6,514,265 B2 | 2/2003 | Ho et al. |
| 6,527,795 B1 | 3/2003 | Lizardi |
| 6,548,002 B2 | 4/2003 | Gresser et al. |
| 6,548,569 B1 | 4/2003 | Williams et al. |
| 6,551,343 B1 | 4/2003 | Tormala et al. |
| 6,554,802 B1 | 4/2003 | Pearson et al. |
| 6,565,597 B1 | 5/2003 | Fearnot et al. |
| 6,592,609 B1 | 7/2003 | Bonutti |
| 6,596,296 B1 | 7/2003 | Nelson et al. |
| 6,599,310 B2 | 7/2003 | Leung et al. |
| 6,607,541 B1 | 8/2003 | Gardiner et al. |
| 6,610,078 B1 | 8/2003 | Bru-Magniez et al. |
| 6,613,059 B2 | 9/2003 | Schaller et al. |
| 6,613,254 B1 | 9/2003 | Shiffer |
| 6,616,982 B2 | 9/2003 | Merrill et al. |
| 6,623,492 B1 | 9/2003 | Berube et al. |
| 6,626,930 B1 | 9/2003 | Allen et al. |
| 6,632,245 B2 | 10/2003 | Kim |
| 6,641,592 B1 | 11/2003 | Sauer et al. |
| 6,641,593 B1 | 11/2003 | Schaller et al. |
| 6,645,226 B1 | 11/2003 | Jacobs et al. |
| 6,645,227 B2 | 11/2003 | Fallin et al. |
| 6,645,228 B2 | 11/2003 | Renz |
| 6,648,921 B2 | 11/2003 | Anderson et al. |
| 6,656,182 B1 | 12/2003 | Hayhurst |
| 6,689,153 B1 | 2/2004 | Skiba |
| 6,689,166 B2 | 2/2004 | Laurencin et al. |
| 6,692,761 B2 | 2/2004 | Mahmood et al. |
| 6,702,844 B1 | 3/2004 | Lazarus |
| 6,712,830 B2 | 3/2004 | Esplin |
| 6,712,859 B2 * | 3/2004 | Rousseau et al. ........... 623/23.64 |
| 6,716,234 B2 | 4/2004 | Grafton et al. |
| 6,720,402 B2 | 4/2004 | Langer et al. |
| 6,726,705 B2 | 4/2004 | Peterson et al. |
| 6,746,443 B1 | 6/2004 | Morley et al. |
| 6,746,458 B1 | 6/2004 | Cloud |
| 6,749,616 B1 | 6/2004 | Nath |
| 6,773,450 B2 | 8/2004 | Leung et al. |
| 6,783,554 B2 | 8/2004 | Amara et al. |
| 6,814,748 B1 | 11/2004 | Baker et al. |
| 6,818,010 B2 | 11/2004 | Eichhorn et al. |
| 6,838,493 B2 | 1/2005 | Williams et al. |
| 6,848,152 B2 | 2/2005 | Genova et al. |
| 6,852,825 B2 | 2/2005 | Ledlein et al. |
| 6,858,222 B2 | 2/2005 | Nelson et al. |
| 6,860,891 B2 | 3/2005 | Schulze |
| 6,860,901 B1 | 3/2005 | Baker et al. |
| 6,867,248 B1 | 3/2005 | Martin et al. |
| 6,877,934 B2 | 4/2005 | Gainer |
| 6,881,766 B2 | 4/2005 | Hain |
| 6,893,452 B2 | 5/2005 | Jacobs |
| 6,905,484 B2 | 6/2005 | Buckman et al. |
| 6,911,035 B1 | 6/2005 | Blomme |
| 6,911,037 B2 | 6/2005 | Gainor et al. |
| 6,913,607 B2 | 7/2005 | Ainsworth et al. |
| 6,921,811 B2 | 7/2005 | Zamora et al. |
| 6,923,819 B2 | 8/2005 | Meade et al. |
| 6,945,021 B2 | 9/2005 | Michel |
| 6,945,980 B2 | 9/2005 | Nguyen et al. |

(56) References Cited

U.S. PATENT DOCUMENTS

| | | | |
|---|---|---|---|
| 6,960,221 B2 | 11/2005 | Ho et al. |
| 6,960,233 B1 | 11/2005 | Berg et al. |
| 6,974,450 B2 | 12/2005 | Weber et al. |
| 6,981,983 B1 | 1/2006 | Rosenblatt et al. |
| 6,984,241 B2 | 1/2006 | Lubbers et al. |
| 6,986,780 B2 | 1/2006 | Rudnick et al. |
| 6,991,643 B2 | 1/2006 | Saadat |
| 6,996,880 B2 | 2/2006 | Kurtz, Jr. et al. |
| 7,021,316 B2 | 4/2006 | Leiboff |
| 7,033,379 B2 | 4/2006 | Peterson |
| 7,033,603 B2 | 4/2006 | Nelson et al. |
| 7,037,984 B2 | 5/2006 | Lendlein et al. |
| 7,048,748 B1 | 5/2006 | Ustuner |
| 7,056,331 B2 | 6/2006 | Kaplan et al. |
| 7,056,333 B2 | 6/2006 | Walshe |
| 7,057,135 B2 | 6/2006 | Li |
| 7,063,716 B2 | 6/2006 | Cunningham |
| 7,070,610 B2 | 7/2006 | Im et al. |
| 7,081,135 B2 | 7/2006 | Smith et al. |
| 7,083,637 B1 | 8/2006 | Tannhauser |
| 7,083,648 B2 | 8/2006 | Yu et al. |
| 7,107,090 B2 | 9/2006 | Salisbury, Jr. et al. |
| 7,112,214 B2 | 9/2006 | Peterson et al. |
| 7,125,403 B2 | 10/2006 | Julian et al. |
| 7,125,413 B2 | 10/2006 | Grigoryants et al. |
| D532,107 S | 11/2006 | Peterson et al. |
| 7,138,441 B1 | 11/2006 | Zhang |
| 7,141,302 B2 | 11/2006 | Mueller et al. |
| 7,144,401 B2 | 12/2006 | Yamamoto et al. |
| 7,144,412 B2 | 12/2006 | Wolf et al. |
| 7,144,415 B2 | 12/2006 | DelRio et al. |
| 7,150,757 B2 | 12/2006 | Fallin et al. |
| 7,156,858 B2 | 1/2007 | Schuldt-Hempe et al. |
| 7,156,862 B2 | 1/2007 | Jacobs et al. |
| 7,160,312 B2 | 1/2007 | Saadat |
| 7,166,570 B2 | 1/2007 | Hunter et al. |
| 7,172,595 B1 | 2/2007 | Goble |
| 7,172,615 B2 | 2/2007 | Morriss et al. |
| 7,186,262 B2 | 3/2007 | Saadat |
| 7,195,634 B2 | 3/2007 | Schmieding et al. |
| 7,211,088 B2 | 5/2007 | Grafton et al. |
| 7,214,230 B2 | 5/2007 | Brock et al. |
| 7,217,744 B2 | 5/2007 | Lendlein et al. |
| 7,225,512 B2 | 6/2007 | Genova et al. |
| 7,226,468 B2 | 6/2007 | Ruff |
| 7,232,447 B2 | 6/2007 | Gellman et al. |
| 7,244,270 B2 | 7/2007 | Lesh et al. |
| 7,279,612 B1 | 10/2007 | Heaton et al. |
| 7,297,142 B2 | 11/2007 | Brock |
| 7,322,105 B2 | 1/2008 | Lewis |
| 7,371,253 B2 | 5/2008 | Leung et al. |
| 7,468,068 B2 * | 12/2008 | Kolster .................... 606/228 |
| 7,513,904 B2 | 4/2009 | Sulamanidze et al. |
| 7,514,095 B2 | 4/2009 | Nelson et al. |
| 7,582,105 B2 * | 9/2009 | Kolster .................... 606/228 |
| 7,601,164 B2 | 10/2009 | Wu |
| 7,624,487 B2 | 12/2009 | Trull et al. |
| 7,645,293 B2 | 1/2010 | Martinek et al. |
| 7,806,908 B2 | 10/2010 | Ruff |
| 7,845,356 B2 | 12/2010 | Paraschac et al. |
| 7,857,829 B2 | 12/2010 | Kaplan et al. |
| 7,879,072 B2 | 2/2011 | Bonutti et al. |
| 7,919,112 B2 | 4/2011 | Pathak et al. |
| 8,118,834 B1 | 2/2012 | Goraltchouk et al. |
| 8,216,273 B1 | 7/2012 | Goraltchouk et al. |
| 8,226,684 B2 * | 7/2012 | Nawrocki et al. .......... 606/228 |
| 8,308,761 B2 | 11/2012 | Brailovski et al. |
| 2001/0011187 A1 | 8/2001 | Pavcnik et al. |
| 2001/0018592 A1 | 8/2001 | Schaller et al. |
| 2001/0018599 A1 | 8/2001 | D'Aversa et al. |
| 2001/0039450 A1 | 11/2001 | Pavcnik et al. |
| 2001/0044637 A1 | 11/2001 | Jacobs et al. |
| 2001/0051807 A1 | 12/2001 | Grafton |
| 2001/0051815 A1 | 12/2001 | Esplin |
| 2002/0007218 A1 | 1/2002 | Cauthen |
| 2002/0022861 A1 | 2/2002 | Jacobs et al. |
| 2002/0029011 A1 | 3/2002 | Dyer |
| 2002/0029066 A1 | 3/2002 | Foerster |
| 2002/0069617 A1 | 6/2002 | Dey et al. |
| 2002/0077448 A1 | 6/2002 | Antal et al. |
| 2002/0077631 A1 | 6/2002 | Lubbers et al. |
| 2002/0095164 A1 | 7/2002 | Andreas et al. |
| 2002/0099394 A1 | 7/2002 | Houser et al. |
| 2002/0111641 A1 | 8/2002 | Peterson et al. |
| 2002/0111688 A1 | 8/2002 | Cauthen |
| 2002/0138009 A1 | 9/2002 | Brockway et al. |
| 2002/0151932 A1 | 10/2002 | Bryant et al. |
| 2002/0151980 A1 | 10/2002 | Cauthen |
| 2002/0161168 A1 | 10/2002 | Shalaby et al. |
| 2002/0173807 A1 | 11/2002 | Jacobs |
| 2002/0173822 A1 | 11/2002 | Justin et al. |
| 2002/0179718 A1 | 12/2002 | Murokh et al. |
| 2003/0014077 A1 | 1/2003 | Leung et al. |
| 2003/0040795 A1 | 2/2003 | Elson et al. |
| 2003/0041426 A1 | 3/2003 | Genova et al. |
| 2003/0065360 A1 | 4/2003 | Jacobs et al. |
| 2003/0065402 A1 | 4/2003 | Anderson et al. |
| 2003/0069602 A1 | 4/2003 | Jacobs et al. |
| 2003/0074021 A1 | 4/2003 | Morriss et al. |
| 2003/0074023 A1 | 4/2003 | Kaplan et al. |
| 2003/0078604 A1 | 4/2003 | Walshe |
| 2003/0088270 A1 | 5/2003 | Lubbers et al. |
| 2003/0097150 A1 | 5/2003 | Fallin et al. |
| 2003/0105489 A1 | 6/2003 | Eichhorn et al. |
| 2003/0149447 A1 * | 8/2003 | Morency et al. ........... 606/228 |
| 2003/0158604 A1 | 8/2003 | Cauthen, III et al. |
| 2003/0167072 A1 | 9/2003 | Oberlander |
| 2003/0199923 A1 | 10/2003 | Khairkhahan et al. |
| 2003/0203003 A1 | 10/2003 | Nelson et al. |
| 2003/0204193 A1 | 10/2003 | Gabriel et al. |
| 2003/0204195 A1 | 10/2003 | Keane et al. |
| 2003/0225424 A1 | 12/2003 | Benderev |
| 2003/0229361 A1 | 12/2003 | Jackson |
| 2003/0236550 A1 | 12/2003 | Peterson et al. |
| 2003/0236551 A1 | 12/2003 | Peterson |
| 2004/0006353 A1 | 1/2004 | Bosley, Jr. et al. |
| 2004/0010275 A1 | 1/2004 | Jacobs et al. |
| 2004/0010276 A1 | 1/2004 | Jacobs et al. |
| 2004/0015187 A1 | 1/2004 | Lendlein et al. |
| 2004/0024169 A1 | 2/2004 | Shalaby et al. |
| 2004/0024420 A1 | 2/2004 | Lubbers et al. |
| 2004/0028655 A1 | 2/2004 | Nelson et al. |
| 2004/0030354 A1 | 2/2004 | Leung et al. |
| 2004/0039415 A1 | 2/2004 | Zamierowski |
| 2004/0049224 A1 | 3/2004 | Buehlmann et al. |
| 2004/0059370 A1 | 3/2004 | Greene, Jr. et al. |
| 2004/0059377 A1 | 3/2004 | Peterson et al. |
| 2004/0059378 A1 | 3/2004 | Peterson et al. |
| 2004/0060409 A1 | 4/2004 | Leung et al. |
| 2004/0060410 A1 | 4/2004 | Leung et al. |
| 2004/0068293 A1 | 4/2004 | Scalzo et al. |
| 2004/0068294 A1 | 4/2004 | Scalzo et al. |
| 2004/0088003 A1 | 5/2004 | Leung et al. |
| 2004/0093023 A1 | 5/2004 | Allen et al. |
| 2004/0093028 A1 | 5/2004 | Ruff |
| 2004/0098051 A1 | 5/2004 | Fallin et al. |
| 2004/0106949 A1 | 6/2004 | Cohn et al. |
| 2004/0116620 A1 | 6/2004 | Shalaby et al. |
| 2004/0138683 A1 | 7/2004 | Shelton et al. |
| 2004/0153153 A1 | 8/2004 | Elson et al. |
| 2004/0167572 A1 | 8/2004 | Roth et al. |
| 2004/0167575 A1 | 8/2004 | Roby |
| 2004/0186487 A1 | 9/2004 | Klein et al. |
| 2004/0193191 A1 | 9/2004 | Starksen et al. |
| 2004/0193217 A1 | 9/2004 | Lubbers et al. |
| 2004/0193257 A1 | 9/2004 | Wu et al. |
| 2004/0226427 A1 | 11/2004 | Trull et al. |
| 2004/0230223 A1 | 11/2004 | Bonutti et al. |
| 2004/0237736 A1 | 12/2004 | Genova et al. |
| 2004/0254609 A1 | 12/2004 | Esplin |
| 2004/0260340 A1 | 12/2004 | Jacobs et al. |
| 2004/0265282 A1 | 12/2004 | Wright et al. |
| 2004/0267309 A1 | 12/2004 | Garvin |
| 2005/0004601 A1 | 1/2005 | Kong et al. |

(56) References Cited

U.S. PATENT DOCUMENTS

| | | |
|---|---|---|
| 2005/0004602 A1 | 1/2005 | Hart et al. |
| 2005/0033324 A1 | 2/2005 | Phan |
| 2005/0033367 A1 | 2/2005 | Leung et al. |
| 2005/0034431 A1 | 2/2005 | Dey et al. |
| 2005/0038472 A1 | 2/2005 | Furst |
| 2005/0049636 A1 | 3/2005 | Leiboff |
| 2005/0055051 A1 | 3/2005 | Grafton |
| 2005/0059984 A1 | 3/2005 | Chanduszko et al. |
| 2005/0065533 A1 | 3/2005 | Magen et al. |
| 2005/0070959 A1 | 3/2005 | Cichocki, Jr. |
| 2005/0080455 A1 | 4/2005 | Schmieding et al. |
| 2005/0085857 A1 | 4/2005 | Peterson et al. |
| 2005/0096698 A1 | 5/2005 | Lederman |
| 2005/0106211 A1 | 5/2005 | Nelson et al. |
| 2005/0113936 A1 | 5/2005 | Brustad et al. |
| 2005/0119694 A1 | 6/2005 | Jacobs et al. |
| 2005/0125020 A1 | 6/2005 | Meade et al. |
| 2005/0125034 A1 | 6/2005 | Cichocki, Jr. |
| 2005/0125035 A1 | 6/2005 | Cichocki, Jr. |
| 2005/0149064 A1 | 7/2005 | Peterson et al. |
| 2005/0149118 A1 | 7/2005 | Koyfman et al. |
| 2005/0154255 A1 | 7/2005 | Jacobs |
| 2005/0171561 A1 | 8/2005 | Songer et al. |
| 2005/0177190 A1 | 8/2005 | Zamierowski |
| 2005/0181009 A1 | 8/2005 | Hunter et al. |
| 2005/0182444 A1 | 8/2005 | Peterson et al. |
| 2005/0182445 A1 | 8/2005 | Zamierowski |
| 2005/0186247 A1 | 8/2005 | Hunter et al. |
| 2005/0197699 A1 | 9/2005 | Jacobs et al. |
| 2005/0199249 A1 | 9/2005 | Karram |
| 2005/0203576 A1* | 9/2005 | Sulamanidze et al. ........ 606/228 |
| 2005/0209542 A1 | 9/2005 | Jacobs et al. |
| 2005/0209612 A1 | 9/2005 | Nakao |
| 2005/0234510 A1 | 10/2005 | Zamierowski |
| 2005/0240220 A1 | 10/2005 | Zamierowski |
| 2005/0240224 A1 | 10/2005 | Wu |
| 2005/0267531 A1 | 12/2005 | Ruff et al. |
| 2005/0267532 A1 | 12/2005 | Wu |
| 2005/0277984 A1 | 12/2005 | Long |
| 2005/0283246 A1 | 12/2005 | Cauthen, III et al. |
| 2006/0020272 A1 | 1/2006 | Gildenberg |
| 2006/0030884 A1 | 2/2006 | Young et al. |
| 2006/0036266 A1 | 2/2006 | Sulamanidze et al. |
| 2006/0058470 A1 | 3/2006 | Rizk |
| 2006/0058574 A1 | 3/2006 | Priewe et al. |
| 2006/0058799 A1 | 3/2006 | Elson et al. |
| 2006/0058844 A1 | 3/2006 | White et al. |
| 2006/0063476 A1 | 3/2006 | Dore |
| 2006/0064115 A1 | 3/2006 | Allen et al. |
| 2006/0064116 A1 | 3/2006 | Allen et al. |
| 2006/0064127 A1 | 3/2006 | Fallin et al. |
| 2006/0079469 A1 | 4/2006 | Anderson et al. |
| 2006/0079935 A1 | 4/2006 | Kolster |
| 2006/0085016 A1 | 4/2006 | Eremia |
| 2006/0089525 A1 | 4/2006 | Mamo et al. |
| 2006/0089672 A1 | 4/2006 | Martinek |
| 2006/0111734 A1 | 5/2006 | Kaplan et al. |
| 2006/0111742 A1 | 5/2006 | Kaplan et al. |
| 2006/0116503 A1 | 6/2006 | Lendlein et al. |
| 2006/0122608 A1 | 6/2006 | Fallin et al. |
| 2006/0135994 A1 | 6/2006 | Ruff |
| 2006/0135995 A1 | 6/2006 | Ruff |
| 2006/0140999 A1 | 6/2006 | Lendlein et al. |
| 2006/0142784 A1 | 6/2006 | Kontos |
| 2006/0193769 A1 | 8/2006 | Nelson et al. |
| 2006/0194721 A1 | 8/2006 | Allen |
| 2006/0200062 A1 | 9/2006 | Saadat |
| 2006/0207612 A1 | 9/2006 | Jackson et al. |
| 2006/0229671 A1 | 10/2006 | Steiner et al. |
| 2006/0235445 A1 | 10/2006 | Birk et al. |
| 2006/0235447 A1 | 10/2006 | Walshe |
| 2006/0235516 A1 | 10/2006 | Cavazzoni |
| 2006/0241658 A1 | 10/2006 | Cerundolo |
| 2006/0249405 A1 | 11/2006 | Cerwin et al. |
| 2006/0253126 A1 | 11/2006 | Bjerken et al. |
| 2006/0257629 A1 | 11/2006 | Ledlein et al. |
| 2006/0258938 A1 | 11/2006 | Hoffman et al. |
| 2006/0272979 A1 | 12/2006 | Lubbers et al. |
| 2006/0276808 A1 | 12/2006 | Arnal et al. |
| 2006/0282099 A1 | 12/2006 | Stokes et al. |
| 2006/0286289 A1 | 12/2006 | Prajapati et al. |
| 2006/0287675 A1 | 12/2006 | Prajapati et al. |
| 2006/0287676 A1 | 12/2006 | Prajapati et al. |
| 2006/0293710 A1 | 12/2006 | Foerster et al. |
| 2007/0005109 A1 | 1/2007 | Popadiuk et al. |
| 2007/0005110 A1 | 1/2007 | Collier et al. |
| 2007/0021779 A1 | 1/2007 | Garvin et al. |
| 2007/0027475 A1 | 2/2007 | Pagedas |
| 2007/0038249 A1* | 2/2007 | Kolster ........................ 606/228 |
| 2007/0065663 A1 | 3/2007 | Trull et al. |
| 2007/0088135 A1 | 4/2007 | Lendlein et al. |
| 2007/0088391 A1 | 4/2007 | McAlexander et al. |
| 2007/0134292 A1 | 6/2007 | Suokas et al. |
| 2007/0135840 A1 | 6/2007 | Schmieding |
| 2007/0135843 A1 | 6/2007 | Burkhart |
| 2007/0151961 A1 | 7/2007 | Kleine et al. |
| 2007/0156175 A1 | 7/2007 | Weadock et al. |
| 2007/0167958 A1 | 7/2007 | Sulamanidze et al. |
| 2007/0187861 A1 | 8/2007 | Geneva et al. |
| 2007/0208355 A1 | 9/2007 | Ruff |
| 2007/0208377 A1 | 9/2007 | Kaplan et al. |
| 2007/0219587 A1 | 9/2007 | Accardo |
| 2007/0224237 A1 | 9/2007 | Hwang et al. |
| 2007/0225642 A1 | 9/2007 | Houser et al. |
| 2007/0225761 A1 | 9/2007 | Shetty |
| 2007/0227914 A1 | 10/2007 | Cerwin et al. |
| 2007/0233188 A1 | 10/2007 | Hunt et al. |
| 2007/0239206 A1 | 10/2007 | Shelton, IV et al. |
| 2007/0239207 A1 | 10/2007 | Beramendi |
| 2007/0257395 A1 | 11/2007 | Lindh et al. |
| 2007/0282247 A1 | 12/2007 | Desai et al. |
| 2007/0293892 A1 | 12/2007 | Takasu |
| 2008/0004490 A1 | 1/2008 | Bosley, Jr. et al. |
| 2008/0004603 A1 | 1/2008 | Larkin et al. |
| 2008/0009838 A1 | 1/2008 | Schena et al. |
| 2008/0009888 A1 | 1/2008 | Ewers et al. |
| 2008/0009902 A1 | 1/2008 | Hunter et al. |
| 2008/0027273 A1 | 1/2008 | Gutterman |
| 2008/0027486 A1 | 1/2008 | Jones et al. |
| 2008/0046094 A1 | 2/2008 | Han et al. |
| 2008/0058869 A1 | 3/2008 | Stopek et al. |
| 2008/0064839 A1 | 3/2008 | Hadba et al. |
| 2008/0066764 A1 | 3/2008 | Paraschac et al. |
| 2008/0066765 A1 | 3/2008 | Paraschac et al. |
| 2008/0066766 A1 | 3/2008 | Paraschac et al. |
| 2008/0066767 A1 | 3/2008 | Paraschac et al. |
| 2008/0077181 A1 | 3/2008 | Jones et al. |
| 2008/0082113 A1 | 4/2008 | Bishop et al. |
| 2008/0082129 A1 | 4/2008 | Jones et al. |
| 2008/0086169 A1 | 4/2008 | Jones et al. |
| 2008/0086170 A1 | 4/2008 | Jones et al. |
| 2008/0109036 A1 | 5/2008 | Stopek et al. |
| 2008/0131692 A1 | 6/2008 | Rolland et al. |
| 2008/0132943 A1 | 6/2008 | Maiorino et al. |
| 2008/0169059 A1 | 7/2008 | Messersmith et al. |
| 2008/0195147 A1 | 8/2008 | Stopek |
| 2008/0195417 A1 | 8/2008 | Surpin et al. |
| 2008/0208358 A1 | 8/2008 | Bellamkonda et al. |
| 2008/0215072 A1 | 9/2008 | Kelly |
| 2008/0221618 A1 | 9/2008 | Chen et al. |
| 2008/0234731 A1 | 9/2008 | Leung et al. |
| 2008/0248216 A1 | 10/2008 | Yeung et al. |
| 2008/0255611 A1 | 10/2008 | Hunter |
| 2008/0262542 A1 | 10/2008 | Sulamanidze et al. |
| 2008/0281338 A1 | 11/2008 | Wohlert et al. |
| 2008/0281357 A1 | 11/2008 | Sung et al. |
| 2008/0312688 A1 | 12/2008 | Nawrocki et al. |
| 2009/0012560 A1* | 1/2009 | Hunter et al. ................ 606/228 |
| 2009/0018577 A1 | 1/2009 | Leung et al. |
| 2009/0043336 A1 | 2/2009 | Yuan et al. |
| 2009/0076543 A1 | 3/2009 | Maiorino et al. |
| 2009/0082856 A1 | 3/2009 | Flanagan |
| 2009/0088835 A1 | 4/2009 | Wang |
| 2009/0099597 A1 | 4/2009 | Isse |

(56) References Cited

U.S. PATENT DOCUMENTS

| | | |
|---|---|---|
| 2009/0105753 A1 | 4/2009 | Greenhalgh et al. |
| 2009/0107965 A1 | 4/2009 | D'Agostino |
| 2009/0112236 A1 | 4/2009 | Stopek |
| 2009/0112259 A1 | 4/2009 | D'Agostino |
| 2009/0143819 A1 | 6/2009 | D'Agostino |
| 2009/0200487 A1 | 8/2009 | Maiorino et al. |
| 2009/0210006 A1 | 8/2009 | Cohen et al. |
| 2009/0216253 A1 | 8/2009 | Bell et al. |
| 2009/0226500 A1 | 9/2009 | Avelar et al. |
| 2009/0248066 A1* | 10/2009 | Wilkie ............... 606/228 |
| 2009/0248067 A1 | 10/2009 | Maiorino |
| 2009/0248070 A1 | 10/2009 | Kosa et al. |
| 2009/0250356 A1 | 10/2009 | Kirsch et al. |
| 2009/0250588 A1 | 10/2009 | Robeson et al. |
| 2009/0259233 A1 | 10/2009 | Bogart et al. |
| 2009/0259251 A1 | 10/2009 | Cohen |
| 2009/0287245 A1* | 11/2009 | Ostrovsky et al. ........ 606/228 |
| 2009/0299407 A1 | 12/2009 | Yuan et al. |
| 2009/0299408 A1 | 12/2009 | Schuldt-Hempe et al. |
| 2009/0306710 A1 | 12/2009 | Lindh et al. |
| 2010/0021516 A1 | 1/2010 | McKay |
| 2010/0023055 A1 | 1/2010 | Rousseau |
| 2010/0057123 A1 | 3/2010 | D'Agostino et al. |
| 2010/0063540 A1 | 3/2010 | Maiorino |
| 2010/0071833 A1 | 3/2010 | Maiorino |
| 2010/0087855 A1 | 4/2010 | Leung et al. |
| 2010/0101707 A1 | 4/2010 | Maiorino et al. |
| 2010/0140115 A1 | 6/2010 | Kirsch |
| 2010/0160961 A1* | 6/2010 | Nawrocki et al. ........ 606/228 |
| 2010/0163056 A1 | 7/2010 | Tschopp et al. |
| 2010/0211097 A1 | 8/2010 | Hadba et al. |
| 2010/0211098 A1 | 8/2010 | Hadba et al. |
| 2010/0239635 A1 | 9/2010 | McClain et al. |
| 2010/0292718 A1 | 11/2010 | Sholev et al. |
| 2010/0294103 A1 | 11/2010 | Genova et al. |
| 2010/0294104 A1 | 11/2010 | Genova et al. |
| 2010/0294105 A1 | 11/2010 | Genova et al. |
| 2010/0294106 A1 | 11/2010 | Genova et al. |
| 2010/0294107 A1 | 11/2010 | Genova et al. |
| 2010/0298637 A1 | 11/2010 | Ruff |
| 2010/0298867 A1 | 11/2010 | Ruff |
| 2010/0298868 A1 | 11/2010 | Ruff |
| 2010/0298871 A1 | 11/2010 | Ruff et al. |
| 2010/0298878 A1 | 11/2010 | Leung et al. |
| 2010/0298879 A1 | 11/2010 | Leung et al. |
| 2010/0298880 A1 | 11/2010 | Leung et al. |
| 2010/0313723 A1 | 12/2010 | Genova et al. |
| 2010/0313729 A1 | 12/2010 | Genova et al. |
| 2010/0313730 A1 | 12/2010 | Genova et al. |
| 2010/0318122 A1 | 12/2010 | Leung et al. |
| 2010/0318123 A1 | 12/2010 | Leung et al. |
| 2011/0009902 A1 | 1/2011 | Leung et al. |
| 2011/0046669 A1 | 2/2011 | Goraltchouk et al. |
| 2011/0106152 A1 | 5/2011 | Kozlowski |
| 2011/0130774 A1 | 6/2011 | Criscuolo et al. |
| 2011/0166597 A1 | 7/2011 | Herrmann et al. |
| 2012/0109188 A1 | 5/2012 | Viola |

FOREIGN PATENT DOCUMENTS

| | | |
|---|---|---|
| CN | 2640420 | 9/2004 |
| DE | 01810800 | 6/1970 |
| DE | 03227984 | 2/1984 |
| DE | 04302895 | 8/1994 |
| DE | 19618891 | 4/1997 |
| DE | 19833703 | 2/2000 |
| DE | 10245025 | 4/2004 |
| DE | 102005004317 | 6/2006 |
| EP | 0121362 | 9/1987 |
| EP | 0329787 | 8/1989 |
| EP | 0513713 | 5/1992 |
| EP | 0428253 | 7/1994 |
| EP | 0632999 | 1/1995 |
| EP | 0513736 | 2/1995 |
| EP | 0464479 | 3/1995 |
| EP | 0464480 | 3/1995 |
| EP | 0576337 | 3/1997 |
| EP | 0576337 B1 | 3/1997 |
| EP | 0574707 | 8/1997 |
| EP | 0612504 | 11/1997 |
| EP | 0558993 | 4/1998 |
| EP | 0913123 | 5/1999 |
| EP | 0916310 | 5/1999 |
| EP | 0664198 | 6/1999 |
| EP | 0960600 | 12/1999 |
| EP | 0705567 | 3/2002 |
| EP | 0673624 | 8/2002 |
| EP | 0839499 | 9/2003 |
| EP | 0755656 | 12/2003 |
| EP | 1075843 | 2/2005 |
| EP | 1525851 | 4/2005 |
| EP | 1532942 | 5/2005 |
| EP | 0826337 | 12/2005 |
| EP | 0991359 | 11/2007 |
| EP | 2036502 | 3/2009 |
| EP | 1948261 | 11/2010 |
| EP | 1726317 | 7/2012 |
| EP | 2338421 | 11/2012 |
| FR | 2619129 | 2/1989 |
| FR | 2693108 | 1/1994 |
| FR | 9208059 | 3/1997 |
| GB | 0267007 | 3/1927 |
| GB | 1091282 | 11/1967 |
| GB | 1428560 | 7/1973 |
| GB | 1506362 | 4/1978 |
| GB | 1508627 | 4/1978 |
| JP | 1506362 | 4/1978 |
| JP | 054116419 | 9/1979 |
| JP | 63288146 | 11/1988 |
| JP | 001113091 | 5/1989 |
| JP | 003-165751 | 7/1991 |
| JP | 4-096758 | 3/1992 |
| JP | 004-266749 | 9/1992 |
| JP | 9-103477 | 4/1997 |
| JP | 410085225 | 4/1998 |
| JP | 11-313826 | 11/1999 |
| JP | 011332828 | 12/1999 |
| JP | 2002-59235 | 2/2002 |
| JP | 2003-275217 | 9/2003 |
| JP | 2009-118967 | 6/2009 |
| KR | 10-2005-0072908 A | 7/2005 |
| KR | 6013299 | 2/2006 |
| KR | 2006-59142 | 6/2006 |
| NZ | 501224 | 3/2002 |
| NZ | 531262 | 12/2005 |
| RU | 1823791 | 6/1993 |
| RU | 2139690 | 10/1999 |
| RU | 2175855 | 11/2001 |
| RU | 2241389 | 12/2004 |
| RU | 2268752 | 1/2006 |
| SU | 1745214 | 7/1992 |
| SU | 1752358 | 8/1992 |
| WO | WO 96/06565 | 3/1966 |
| WO | WO 86/00020 | 1/1986 |
| WO | WO 87/01270 | 3/1987 |
| WO | WO 88/09157 | 12/1988 |
| WO | WO 89/05618 | 6/1989 |
| WO | WO 90/09149 | 8/1990 |
| WO | WO 90/14795 | 12/1990 |
| WO | WO 92/22336 | 12/1992 |
| WO | WO 95/16399 | 6/1995 |
| WO | WO 95/29637 | 11/1995 |
| WO | WO 98/52473 | 11/1998 |
| WO | WO 98/55031 | 12/1998 |
| WO | WO 99/21488 | 5/1999 |
| WO | WO 99/33401 | 7/1999 |
| WO | WO 99/52478 | 10/1999 |
| WO | WO 99/59477 | 11/1999 |
| WO | WO 99/62431 | 12/1999 |
| WO | WO 00/51658 | 9/2000 |
| WO | WO 00/51685 | 9/2000 |
| WO | WO 01/06952 | 2/2001 |
| WO | WO 01/56626 | 8/2001 |

(56) References Cited

FOREIGN PATENT DOCUMENTS

| | | |
|---|---|---|
| WO | WO 03/001979 | 1/2003 |
| WO | WO 03/003925 | 1/2003 |
| WO | WO 03/017850 | 3/2003 |
| WO | WO 03/045255 | 6/2003 |
| WO | WO 03/077772 | 9/2003 |
| WO | WO 03/092758 | 11/2003 |
| WO | WO 03/103733 | 12/2003 |
| WO | WO 03/103972 | 12/2003 |
| WO | WO 03/105703 | 12/2003 |
| WO | WO 2004/014236 | 2/2004 |
| WO | WO 2004/030517 | 4/2004 |
| WO | WO 2004/030520 | 4/2004 |
| WO | WO 2004/030704 | 4/2004 |
| WO | WO 2004/030705 | 4/2004 |
| WO | WO 2004/062459 | 7/2004 |
| WO | WO 2004/100801 | 11/2004 |
| WO | WO 2004/112853 | 12/2004 |
| WO | WO 2005/016176 | 2/2005 |
| WO | WO 2005/074913 | 8/2005 |
| WO | WO 2005/096955 | 10/2005 |
| WO | WO 2005/096956 | 10/2005 |
| WO | WO 2005/112787 | 12/2005 |
| WO | WO 2006/005144 | 1/2006 |
| WO | WO 2006/012128 | 2/2006 |
| WO | WO 2006/061868 | 6/2006 |
| WO | WO 2006/079469 | 8/2006 |
| WO | WO 2006/082060 | 8/2006 |
| WO | WO 2006/099703 | 9/2006 |
| WO | WO 2006/138300 | 12/2006 |
| WO | WO 2007/005291 | 1/2007 |
| WO | WO 2007/005296 | 1/2007 |
| WO | WO 2007/038837 | 4/2007 |
| WO | WO 2007/053812 | 5/2007 |
| WO | WO 2007/089864 | 8/2007 |
| WO | WO 2007/112024 | 10/2007 |
| WO | WO 2007/133103 | 11/2007 |
| WO | WO 2007/145614 | 12/2007 |
| WO | WO 2008/020937 | 2/2008 |
| WO | WO 2008/128113 | 10/2008 |
| WO | WO 2008/150773 | 12/2008 |
| WO | WO 2009/042841 | 4/2009 |
| WO | WO 2009/068252 | 6/2009 |
| WO | WO 2009/087105 | 7/2009 |
| WO | WO 2009/097556 | 8/2009 |
| WO | WO 2009/151876 | 12/2009 |
| WO | WO 2010/052007 | 5/2010 |
| WO | WO 2011/053375 | 5/2011 |

OTHER PUBLICATIONS

US 6,503,260, (withdrawn).
Bacci, Pier Antonio, "Chirurgia Estetica Mini Invasiva Con Fili Di Sostegno", Collana di Arti, Pensiero e Scienza; Minelli Editore—2006; 54 pgs.
Behl, Marc et al., "Shape-Memory Polymers", Materials Today Apr. 2007; 10(4); 20-28.
Belkas, J. S. et al., "Peripheral nerve regeneration through a synthetic hydrogel nerve tube", Restorative Neurology and Neuroscience 23 (2005) 19-29.
Bellin, I. et al., "Polymeric triple-shape materials", Proceedings of the National Academy of Sciences of the United States of America Nov. 28, 2006; 2103(48):18043-18047.
Boenisch, U.W. et al 'Pull-Out strength and stiffness of meniscal repair using absorbable arrows or Ti-Cron vertical and horizontal loop sutures' American Journal of Sports Medicine, Sep.-Oct. (1999) vol. 27, Issue 5, pp. 626-631.
Buckley, P.R. 'Actuation of Shape Memory Polymer using Magnetic Fields for Applications in Medical Devices' Master of Science in Mechanical Engineering in Massachusetts Institute of Technology Jun. 2003, 144 pages.
Buncke, Jr., H.J. et al 'The Suture Repair of One-Millimeter Vessels, microvascular surgery' (1966) Report of First Conference; Oct. 6-7 pp. 24-35.

Bunnell, S. 'Gig pull-out suture for tendons' J Bone Joint Surg Am (1954) vol. 36A, No. 4 pp. 850-851.
CCPR Centro De Cirurgia Plastica e Reabilitacao 'Up Lifting (Aptos Threads) http://ccpr.com.br/upl-l.htm, Aug. 19, 2002 pp. 1-2.
Dahlin, Lars, "Techniques of Peripheral Nerve Repair", Scandinavian Journal of Surgery 97: 310-316, 2008.
Datillo, Jr. P.P. et al 'Medical Textiles: Application of an Absorbable Barbed Bi-Directional Surgical Suture' (2002) The Journal of Textile and Apparel Technology and Management vol. 2, Issue 2, pp. 1-5.
Datillo, Jr., P. et al 'Tissue holding performance of knotless absorbable sutures' Society for Biomaterials 29th Annual Meeting Transactions (2001 or 2003??) p. 101.
Declaration of Dr. Gregory L. Ruff, dated Aug. 19, 2005, 8 pages, with Exhibits A-E.
De Persia, Raúl et al., "Mechanics of Biomaterials: Sutures After the Surgery", Applications of Engineering Mechanics in Medicine, GED-University of Puerto Rico, Mayaguez May 2005, p. F1-F27.
Delorenzi, C.L., "Barbed Sutures: Rationale and Technique", Aesthetic Surg J. Mar. 26, 2006(2): 223-229.
Demyttenaere, Sebastian V. et al., "Barbed Suture for Gastrointestinal Closure: A Randomized Control Trial", Surgical Innovation; vol. 16, No. 3; Sep. 2009; pp. 237-242.
Einarsson, Jon I. et al., "Barbed Suture, now in the toolbox of minimally invasive gyn surgery", OBG Management; vol. 21, No. 9; Sep. 2009; pp. 39-41.
Gross, Alex, "Physician perspective on thread lifts", Dermatology Times Feb. 27, 2006(2): 2 pages.
Han, H. et al 'Mating and Piercing Micromechanical Suture for Surface Bonding Applications' (1991) Proceedings of the 1991 Micro Electro Mechanical Systems (MEMS>91), an Investigation of Micro Structures, Sensors, Actuators, Machines and Robots pp. 253-258.
Ingle, N. P. et al 'Barbed Suture Anchoring Strength: Applicability to Dissimilar Polymeric Materials' College of Textiles, North Carolina State University, 7th World Biomaterials Congress 2004, 1 page.
Ingle, N. P. et al 'Mechanical Performance and Finite Element Analysis of Bi-directional Barbed Sutures' Master of Science in Textile Technology & Management at North Carolina State University Aug. 2003, 126 pages.
Ingle, N. P. et al., "Optimizing the tissue anchoring performance of barbed sutures in skin and tendon tissues", Journal of Biomechanics 43 (2010); pp. 302-309.
Ingle, Nilesh P et al., "Testing the Tissue-holding Capacity of Barbed Sutures", College of Textiles, North Carolina State University, Fiber Science, the Next Generation Oct. 17-19, 2005, New Jersey Institute of Technology, Newark, NJ, 4 pages.
Jennings et al 'A New Technique in primary tendon repair' Surg Gynecol Obstet (1952) vol. 95, No. 5 pp. 597-600.
Kaminer, M. et al., "ContourLift™: A New Method of Minimally Invasive Facial Rejuvenation", Cosmetic Dermatology Jan. 2007; 20(1): 29-35.
Kelch et al., "Shape-memory Polymer Networks from Olio[(0-hydroxycaproate)-co-glycolate]dimethacrylates and Butyl Acrylate with Adjustable Hydrolytic Degradation Rate", Biomacromolecules 2007;8(3):1018-1027.
Khademhosseini, Ali et al., "Nanobiotechnology Drug Delivery and Tissue Engineering", Chemical Engineering Progress 102:38-42 (2006).
Kuniholm J.F. et al 'Automated Knot Tying for Fixation in Minimally Invasive, Robot Assisted Cardiac Surgery' Master of Science in Mechanical & Aerospace Engineering at North Carolina State University May 2003, 71 pages.
Lendelin, A. et al 'Biodegradable, Elastic Shape-Memory Polymers for Potential Biomedical Applications' (2002) Science vol. 296 pp. 1673-1676.
Lendelin, A. et al 'Shape-Memory Polymers' Agnew Chem Int. Ed. (2002) vol. 41 pp. 2034-2057.
Leung, J. et al 'Barbed, Bi-directional Medical Sutures: Biomechanical Properties and Wound Closure Efficacy Study' 2002 Society for Biomaterials 28th Annual Meeting Transactions 1 page.
Leung, J. et al 'Barbed, Bi-directional Surgical Sutures' International Conference & Exhibition on Healthcare & Medical Textiles, Jul. 8-9, 2003 pp. 1-8.

(56) References Cited

OTHER PUBLICATIONS

Leung, J. et al 'Barbed, Bi-directional Surgical Sutures: in Vivo Strength and Histopathology Evaluations' 2003 Society for Biomaterials 29th Annual Meeting Transactions pp. 100.

Leung, J. et al., "Barbed Suture Technology: Recent Advances", Medical Textiles 2004, Advances in Biomedical Textiles and Healthcare Products, Conference Proceedings, IFAI Expo 2004, Oct. 26-27, 2004, Pittsburgh, PA., pp. 62-80.

Leung, J. et al 'Performance Enhancement of a Knotless Suture via Barb Geometry Modifications' 7th World Biomaterials Congress 2004, 1 page.

Li, Y.Y. et al 'Polymer Replicas of Photonic Porous Silicon for Sensing and Drug Delivery Applications' (2003) Science vol. 299 pp. 2045-2047.

Liu, Changdeng et al., "Shape Memory Polymer with Improved Shape Recovery", Mater. Res. Soc. Symp. Proc. vol. 855E, 2005 Materials Research Society, pp. W4.7.1-W4.7.6.

Madduri, Srinivas, et al., "Neurotrophic factors release from nerve conduits for peripheral axonal regeneration", European Cells and Materials vol. 16; Suppl. 1 (2008), p. 14.

Maitland et al., "Prototype laser-activated shape memory polymer foam device for embolic treatment of aneurysms", Journal of Biomedical Optics May/Jun. 2007;12(3): pp. 030504-1 to 030504-3.

Malina, M. et al 'Endovascular AAA Exclusion: Will Stents with Hooks and Barbs Prevent Stent-Graft Migration' Journal Endovascular Surgery (1998) vol. 5 pp. 310-317.

Mansberger et al 'A New Type Pull-Out Wire for Tendon Surgery: A Preliminary Report' Department of Surgery, University Hospital and University of Maryland School of Medicine, Baltimore, Maryland, Received for Publication May 10, 1951 pp. 119-121.

Mason, M.L. 'Primary and Secondary Tendon Suture. A discussion of the significance of technique in tendon surgery' (1940) Surg Gynecol Obstet 70.

McKee, GK 'Metal anastomosis tubes in tendon suture' The Lancet (1945) pp. 659-660.

McKenzie 'An Experimental Multiple Barbed Suture for the Long Flexor Tendons of the Palm and Fingers' The Journal of Bone and Joint Surgery (1967) vol. 49B, No. 3 pp. 440-447.

Moran et al., "Bidirectional-Barbed Sutured Knotless Running Anastomosis v Classic van Velthovan in a Model System", Journal of Endourology Oct. 2007; 21(10); 1175-1177.

Mullner, "Metal Foam Has a Good Memory", Dec. 18, 2007 Original story at <http://www.physorg.com/news117214996.html>.

Murtha et al., "Evaluation of a Novel Technique for Wound Closure Using a Barbed Suture", Journal of the American Society of Plastic Surgeons 2006; 117(6); 1769-1780.

Nie, Zhihong and Kumacheva, Eugenia, "Patterning surfaces with functional polymers", Nature Materials vol. 7(2008): 277-290.

Paul, Malcolm D. and Rui Avelar, "Quill™ SRS Techniques & Procedures a Novel Approach to Soft Tissue Approximation", Canada, Angiotech Pharmaceuticals, Inc., First Edition 82007: 20 pages.

Paul, Malcolm D. and Rui Avelar, "Quill™ SRS Techniques & Procedures a Novel Approach to Soft Tissue Approximation", Canada, Angiotech Pharmaceuticals, Inc., Fourth Edition 2010, 8 2007-2010: 27 pages.

Paul, Malcolm D. and Rui Avelar, "Quill™ SRS Techniques & Procedures a Novel Approach to Soft Tissue Approximation", Canada, Angiotech Pharmaceuticals, Inc., Second Edition 82008: 20 pages.

Paul, Malcolm D. and Rui Avelar, "Quill™ SRS Techniques & Procedures a Novel Approach to Soft Tissue Approximation", Canada, Angiotech Pharmaceuticals, Inc., Third Edition 2009, 8 2007-2009: 27 pages.

Paul, Malcolm D., "Bidirectional Barbed Sutures for Wound Closure: Evoluation and Applications", Journal of the American College of Certified Wound Specialists (2009) 1, 51-57.

Paul, Malcolm D., "Using Barbed Sutures in Open/Subperiosteal Midface Lifting", Aesthetic Surgery Journal 2006(26): 725-732.

Potenza, A. 'Tendon Healing Within the Flexor Digital Sheath in the Dog: An Experimental Study' Journal of Bone & Joint Surgery (1962) vol. 44A No. 1 pp. 49-64.

Pulvertaft 'Suture Materials and Tendon Junctures' American Journal of Surgery (1965) vol. 109 pp. 346-352.

Quill Medical, Inc. 'Barbed Sutures, wrinkle filters give patients more innovative, nonsurgical options' Press Release of Program presented at American Society of Plastic Surgeons annual scientific meeting; Philadelphia, Oct. 9, 2004 3 pages.

Quill Medical, Inc. 'Quill Medical's Novel-Self-Anchoring Surgical Suture Approved for Sale in Europe' Press Release; Research Triangle Park, N.C. May 10, 2004, 1 page.

Quill Medical, Inc., "Quill Medical, Inc. Receives FDA Clearance for First-in-Class Knot-Less Self-Anchoring Surgical Suture", Press Release; Research Triangle Park, N.C., Nov. 4, 2004, 1 page.

Richert, Ludovic, et al., "Surface Nanopatterning to Control Cell Growth", Advanced Materials 2008(15): 1-5.

Rodeheaver, G.T. et al., "Barbed Sutures for Wound Closure: in Vivo Wound Security, Tissue Compatibility and Cosmesis Measurements", Society for Biomaterials 30th Annual Meeting Transactions, 2005, 2 pages.

Rofin-Baasel 'Laser Marking on Plastic Materials' (2001) RB50.0, Rofin-Baasel Inc. 2 pages.

Ruff, Gregory, "Technique and Uses for Absorbable Barbed Sutures", Aesthetic Surgery Journal Sep./Oct. 2006; 26:620-628.

Scherman, Peter et al., "Sutures as longitudinal guides for the repair of nerve defects—Influence of suture numbers and reconstruction of nerve bifurcations", Restorative Neurology and Neuroscience 23 (2005) 79-85.

Schmid A. et al 'The outspreading anchor cord. A material for arthroscopic suturing of a fresh anterior cruciate ligament rupture' Surgical Clinic of the University of Gottingen'.

Semenov, G.M. et al 'Surgical Suture' (2001) Piter, Saint Petersburg, pp. 12-13 and 92-98.

Serafetinides, AA 'Short pulse laser beam interactions with polymers biocompatible materials and tissue' Proce SPIE vol. 3052 (1996) pp. 111-123.

Sulamanidze, Marlen et al., "APTOS Suture Lifting Methods: 10 Years of Experience", Clin Plastic Surg 36 (2009); pp. 281-306.

Sulamanidze, M.A. et al 'Clinical aspects of bloodless facelift using APTOS filaments' A.V. Vishnevsky Institute of Surgery, Bol=shaya Serpukhovskaya ul, 7, 113811, Moscow, Russia (2002) pp. 24-34.

Sulamanidze, M.A. et al 'Facial lifing with APTOS threads' International Journal of Cosmetic Surgery and Aesthetic Dermatology' (2001) No. 4 pp. 1-8.

Sulamanidze, M.A. et al 'Facial lifing with "APTOS" threads' http://fonendo.com (Jul. 18, 2001) pp. 1-4.

Sulamanidze, M.A. et al 'Management of Facial Rhytids by Subcutaneous Soft Tissue Dissection' (2000) International Journal of Cosmetic Surgery and Aesthetic Dermatology vol. 2 No. 4 pp. 255-259.

Sulamanidze, M.A. et al 'Morphological foundations of facelift using APTOS filaments' Bolshaya Serpukhovskaya ul 27, 113811 Moscow, Russia (2002) pp. 19-26.

Sulamanidze, M.A. et al 'Removal of Facial Soft Tissue Ptosis with Special Threads' Dermatol Surg (2002) vol. 28 pp. 367-371.

Sulamanidze, MD, M.A., et al., "Soft tissue lifting in the mid-face: old philosophy, new approach—internal stitching technique (APTOS NEEDLE)", Plastic and Aesthetic Surgery Clinic TOTAL SHARM, Moscow, Russia, (2005):15-29.

Sulzle, Inc. B.G. et al Drilled End Surgical Needles Jul. 2002 Syracuse, New York.

Surgical Specialties Corporation, "Wound Closure Catalog"; Summer 2005, 5 pages.

Szarmach, R. et al 'An Expanded Surgical Suture and Needle Evaluation and Selection Program by a Healthcare Resource Management Group Purchasing Organization' Journal of Long-Term Effects of Medical Implants (2003) vol. 13 No. 3 pp. 155-170.

Tan Ee Lim et al., "A wireless, passive strain sensor based on the harmonic response of magnetically soft materials", Smart Materials and Structures 17 (2008): pp. 1-6.

Up Lifting (Aptos Threads), http://www.ccpr.com.br/upl-l.htm Aug. 19, 2002 pp. 1-2.

Verdan, C. 'Primary Repair of Flexor Tendons' Journal of Bone and Joint Surgery (1960) vol. 42, No. 4 pp. 647-657.

(56) References Cited

OTHER PUBLICATIONS

Villa, Mark T. et al., "Barbed Sutures: A Review of Literature", Plastic and Reconstructive Surgery; Mar. 2008; vol. 121, No. 3; pp. 102e-108e.
Wu. W. 'Barbed Sutures in Facial Rejuvenation' Aesthetic Surgery Journal (2004) vol. 24 pp. 582-587.
Zoltan, J. 'Cicatrix Optimia: Techniques for Ideal Wound Healing' English language edition University Park Press Baltimore (1977) Chapter 3 pp. 54-55.
Communication from EPO re: 10000486 dated Apr. 4, 2011.
European Search Report re: EP05025816 dated Jun. 23, 2006.
European Search Report for EP07006258.3 dated May 4, 2007, 4 pages.
European Search Report for EP07015906 dated Oct. 2, 2007.
European Search Report for EP07015905.8 dated Oct. 23, 2007, 2 pages.
European Search Report for EP07016222 dated Jan. 7, 2008.
European Search Report for EP10000629.5 dated Mar. 10, 2010, 4 pages.
European Search Report re: EP10000486 dated Apr. 23, 2010.
European Search Report for EP10011871.0 dated Dec. 3, 2010, 2 pages.
European Search Report for EP10011868.6 dated Dec. 6, 2010, 2 pages.
European Search Report for EP10011869 dated Jan. 20, 2011.
European Search Report for EP10186592.1 dated Jan. 19, 2011, 2 pages.
Extended European Search Report re: 07015905.8 dated Oct. 2, 2007.
Extended European Search Report re: 07016222.7 dated Jan. 30, 2008.
International Preliminary Examination Report re: PCT/US1998/10478 dated Dec. 11, 1999.
International Preliminary Report re: PCT/US2009/040545 dated Oct. 19, 2010.
International Search Report for PCT/US1998/10478 dated Sep. 23, 1998.
International Search Report for PCT/US2002/027525 dated Dec. 9, 2002, 3 pages.
International Search Report for PCT/2003/30666 dated Dec. 15, 2004.
International Search Report for PCT/US2003/25088 dated Dec. 29, 2003.
International Search Report for PCT/US2007/074658 dated Jun. 12, 2007, 3 pages.
International Search Report for PCT/US2008/060127 dated Sep. 23, 2008, 5 pages.
International Search Report for PCT/US2008/0064921 dated Nov. 19, 2008, 3 pages.
International Search Report for PCT/US2008/075849 dated Mar. 18, 2009, 4 pages.
International Search Report for PCT/US2009/040545 dated Oct. 29, 2009.
Partial European Search Report re: EP05025816 dated Mar. 20, 2006.
Singapore Search Report for Singapore Patent Application No. 200702625-5 dated Nov. 26, 2008, 7 pages.
Singapore Search Report for Singapore Patent Application No. 200702350-0 dated Nov. 26, 2008, 6 pages.
Singapore Search Report for Singapore Patent Application No. 200703688-2 dated Nov. 26, 2008, 7 pages.
Supplementary European Search Report re: EP98923664 dated Jun. 12, 2001.
Supplementary European Search Report re: EP03785177 dated May 19, 2009.
U.S. Appl. No. 08/859,887, filed May 21, 1997.
U.S. Appl. No. 09/896,455, filed Jun. 29, 2001.
U.S. Appl. No. 09/919,750, filed Jul. 31, 2001.
U.S. Appl. No. 09/943,733, filed Aug. 31, 2001.
U.S. Appl. No. 10/216,516, filed Aug. 9, 2002.
U.S. Appl. No. 10/065,280, filed Sep. 30, 2002.
U.S. Appl. No. 10/065,279, filed Sep. 30, 2002.
U.S. Appl. No. 10/065,278, filed Sep. 30, 2002.
U.S. Appl. No. 10/914,755, filed Aug. 9, 2004.
U.S. Appl. No. 10/941,347, filed Sep. 15, 2004.
U.S. Appl. No. 11/154,230, filed Jun. 16, 2005.
U.S. Appl. No. 11/154,863, filed Jun. 16, 2005.
U.S. Appl. No. 11/307,901, filed Feb. 27, 2006.
U.S. Appl. No. 11/307,900, filed Feb. 27, 2006.
U.S. Appl. No. 11/440,621, filed May 25, 2006.
U.S. Appl. No. 11/440,631, filed May 25, 2006.
U.S. Appl. No. 11/968,494, filed Jan. 2, 2008.
U.S. Appl. No. 11/968,496, filed Jan. 2, 2008.
U.S. Appl. No. 12/119,749, filed May 13, 2008.
U.S. Appl. No. 12/340,530, filed Dec. 19, 2008.
U.S. Appl. No. 12/495,497, filed Jun. 30, 2009.
U.S. Appl. No. 61/357,018, filed Jun. 21, 2010.
U.S. Appl. No. 12/849,960, filed Aug. 4, 2010.
U.S. Appl. No. 12/849,969, filed Aug. 4, 2010.
U.S. Appl. No. 12/849,977, filed Aug. 4, 2010.
U.S. Appl. No. 12/849,983, filed Aug. 4, 2010.
U.S. Appl. No. 12/849,991, filed Aug. 4, 2010.
U.S. Appl. No. 12/850,035, filed Aug. 4, 2010.
U.S. Appl. No. 12/850,063, filed Aug. 4, 2010.
U.S. Appl. No. 13/164,438, filed Jun. 20, 2011.
U.S. Appl. No. 13/335,220, filed Dec. 22, 2011.
European Search Report for EP09014651 dated Jan. 12, 2010.
European Search Report re: 10004453 dated Jun. 15, 2010.
European Search Report for EP10011872 dated Apr. 20, 2011.
European Search Report for EP10012437 dated Apr. 28, 2011.
European Search Report for EP10184766 dated Apr. 20, 2011.
International Preliminary Report re: PCT/US2008/060127 dated Oct. 13, 2009.
International Preliminary Report re: PCT/US2008/087788 dated Jun. 22, 2010.
International Search Report for PCT/US1994/09631 dated Dec. 9, 1994.
International Search Report for PCT/US2002/20449 dated May 20, 2003.
International Search Report for PCT/US2003/030424 dated Nov. 1, 2004.
International Search Report for PCT/US2003/030664 dated May 25, 2004.
International Search Report re: PCT/US2003/030674 dated Sep. 2, 2004.
International Search Report re: PCT/US2004/014962 dated Feb. 24, 2005.
International Search Report for PCT/US2005/017028 dated Mar. 26, 2008.
International Search Report for PCT/US2007/002688 dated Oct. 22, 2007.
International Search Report for PCT/US2008/077813 dated Mar. 31, 2009.
International Search Report for PCT/US2008/082009 dated Feb. 16, 2010.
International Search Report for PCT/US2009/032693 dated Aug. 26, 2009.
International Search Report for PCT/US2009/034703 dated Sep. 28, 2009.
International Search Report for PCT/US2009/063081 dated Aug. 2, 2010.
International Search Report for PCT/US2009/041685 dated Dec. 22, 2009.
International Search Report for PCT/US2009/044274 dated Jan. 15, 2010.
International Search Report for PCT/US2010/056898 dated Aug. 2, 2011.
International Search Report for PCT/US2010/060889 dated Oct. 11, 2011.
International Search Report for PCT/US2011/034660 dated Feb. 8, 2012.
International Search Report for PCT/US2011/035270 dated Jan. 12, 2012.

(56) References Cited

OTHER PUBLICATIONS

International Search Report for PCT/US2011/035271 dated Jan. 12, 2012.
International Search Report re: PCT/US2011/035431 dated Jan. 12, 2012.
International Search Report re: PCT/US2011/040014 dated Feb. 9, 2012.
International Search Report for PCT/US2011/059238 dated May 21, 2012.
International Search Report for PCT/US2011/060069 dated May 18, 2012.
International Search Report for PCT/US2012/030441 dated Sep. 27, 2012.
Supplementary European Search Report re: EP03752630 dated Nov. 17, 2005.
Supplementary European Search Report re: 03770556 dated Nov. 17, 2005.
Supplementary European Search Report re: 03754965 dated Nov. 18, 2005.
Supplementary European Search Report re: 05750101 dated Apr. 7, 2010.
Supplementary European Search Report re: 07017663 dated Nov. 7, 2007.
Encyclopedia of Polymer Science and Engineering, edited by H.F. Mark, et al. Wiley-Interscience, New York, 1989.
Gross, R.A. et al 'Biodegradable Polymers for the Environment' Science 297(5582) 803 (2002).
Immergut, Edmund H., Grulke, Eric A., Abe, Akihiro; Daniel R. 2005 John Wiley & Sons.
Jeong, H.E. et al 'A nontransferring dry adhesive with hierarchial polymer nanohairs' PNAS 106 (14) pp. 5639-5644 (2009).
Madhave et al 'A biodegradable and biocompatible gecko-inspired tissue adhesive' PNAS 105(7) pp. 2307-2312 (2008).
Manual for the Rubber Industry, 2nd ed. Bayer AG, Akron, Ohio, 1993.
Mark, J.E. ed. Physical Properties of Polymers Handbook. American Institute of Physics Press, Woodbury, N.Y., 1996.
Martin, D.P. et al 'Medical applications of poly-4-hydroxybutyrate: a strong flexible absorbable biomaterial' Biochemical Engineering Journal vol. 16 (2003) pp. 97-105.
Middleton and Tipton 'Synthetic Biodegradable Polymers as Medical Devices' (1998) Medical Plastics and Biomaterials Magazine.
Polymer Data Handbook, 1999 by Oxford University Press, Inc.
Polymer Handbook (4th Edition) edited by Brandrup, J. 1999.
The Vanderbilt Rubber Handbook, 3d ed. R.T. Vanderbilt Co., Norwalk, Conn., 1990.

* cited by examiner

SELF-RETAINING SUTURES WITH BI-DIRECTIONAL RETAINERS OR UNI-DIRECTIONAL RETAINERS

FIELD OF THE INVENTION

The present invention relates generally to self-retaining sutures for surgical procedures, methods of manufacturing self-retaining sutures for surgical procedures, and their uses.

BACKGROUND OF INVENTION

Sutures are commonly used for closing or binding together wounds in human or animal tissue, such as skin, muscles, tendons, internal organs, nerves, and blood vessels. Sutures can be formed from non-absorbable material such as silk, nylon, polypropylene, or cotton, or alternatively sutures can be formed from bio-absorbable material such as, but not limited to, homopolymers and/or copolymers of glycolide, lactide, p-dioxanone and ε-caprolactone.

Sutures typically consist of a filamentous suture thread with a needle with a sharp point (attachment of sutures and surgical needles is described in U.S. Pat. Nos. 3,981,307, 5,084,063, 5,102,418, 5,123,911, 5,500,991, 5,722,991, 6,012,216, and 6,163,948, and U.S. Patent Application Publication No. 2004/0088003).

Self-retaining sutures (often referred to as "barbed sutures") differ from conventional sutures in that they possess numerous tiny retainers (often barbs) which anchor into the surrounding tissue following deployment, thereby eliminating the need to tie knots to affix adjacent tissues together, and have been described in, for example, U.S. Pat. No. 6,848,152 and European Patent 1 075 843. Such retainers protrude from the suture periphery and are arranged to allow passage of the self-retaining suture when drawn in one direction (with respect to the direction of protrusion of the retainer) through tissue but resist movement of the self-retaining suture when drawn in the opposite direction. Retainers can reduce slippage of the suture at least in a direction along the suture and can optionally obviate knotting of the suture.

A self-retaining suture may be unidirectional, having one or more retainers oriented in one direction along the length of the suture thread; or bidirectional, typically having one or more retainers oriented in one direction along a portion of the thread, followed by one or more retainers oriented in another (often opposite) direction over the remainder of the thread (as described in the context of barbed retainers in U.S. Pat. Nos. 5,931,855 and 6,241,747). Although any number of sequential or intermittent configurations of retainers are possible, the most common form involves a needle at one end, followed by barbs projecting "away" from the needle until the transition point (often the midpoint) of the suture is reached; at the transition point the configuration of barbs reverses itself 180° (i.e., the barbs are now facing in the opposite direction) along the remaining length of the suture thread before attaching to a second needle at the opposite end. The disclosures of all patents and patent applications mentioned herein are incorporated by reference.

Single-directional self-retaining sutures can include an end that is pointed to allow penetration and passage through tissue when drawn by the end and an opposite end that includes an anchor for engaging tissue at the initial insertion point to limit movement of the suture. Alternatively, bi-directional self-retaining sutures can include retainers grouped and extending in one direction along one portion of the suture and opposing retainers grouped and extending in an opposing direction along another portion of the suture. When implanted so that both groups of retainers are engaging tissue, the retainers can resist movement of the suture through tissue in either direction.

A surgeon may use a surgical needle with an attached suture (which can be a smooth monofilament or can be a multi-filament) to pierce the tissue alternately on opposing faces of a wound to sew the wound closed. Techniques for placement of self-retaining sutures in tissue to close or bind together wounds can include threading the self-retaining suture in straight-line patterns such as zig-zag, and curvilinear patterns such as alpha, sinusoidal, and corkscrew. A surgeon may also use self-retaining sutures to position and support tissue where there is no wound in procedures such as cosmetic surgery of the face, neck, abdominal or thoracic region among others.

More specifically, self-retaining sutures can be used in superficial and deep surgical procedures in humans and animals for closing wounds, repairing traumatic injuries or defects, joining tissues together [bringing severed tissues into approximation, closing an anatomical space, affixing single or multiple tissue layers together, creating anastomoses between two hollow (luminal) structures, adjoining tissues, attaching or reattaching tissues to their proper anatomical location], attaching foreign elements to tissues (affixing medical implants, devices, prostheses and other functional or supportive devices), and for repositioning tissues to new anatomical locations (repairs, tissue elevations, tissue grafting and related procedures) to name but a few examples.

Sutures typically consist of a filamentous suture thread attached to a needle with a sharp point (attachment of sutures and surgical needles is described in U.S. Pat. Nos. 3,981,307, 5,084,063, 5,102,418, 5,123,911, 5,500,991, 5,722,991, 6,012,216, and 6,163,948, and U.S. Patent Application Publication No. US 2004/0088003). Classically, the needle is advanced through the desired tissue on one side of the wound and then through the adjacent side of the wound to form a "loop" which is then completed by tying a knot in the suture.

Sutures materials are broadly classified as being degradable or bioabsorbable (i.e., they break down completely in the body over time), such as those composed of catgut, glycolic acid polymers and copolymers, lactic acid polymers and copolymers, and polyether-esters based copolymers such as polyglycolide or lactide copolymers with polyglycols or polyethers; or as being non-absorbable (permanent; nondegradable), such as those made of polyamide, polytetrafluoroethylene, polyethylene terephthalate, polyurethane, polyether-esters based copolymers such as polybutylene or polyethylene terephthalate with polyglycols or polyethers, metal alloys, metal (e.g., stainless steel wire), polypropylene, polyethelene, silk, and cotton. Degradable (bioabsorbable) sutures have been found to be particularly useful in situations where suture removal might jeopardize the repair or where the natural healing process renders the support provided by the suture material unnecessary after wound healing has been completed; as in, for example, completing an uncomplicated skin closure. Nondegradable (non-absorbable) sutures are used in wounds where healing may be expected to be protracted or where the suture material is needed to provide physical support to the wound for long periods of time; as in, for example, deep tissue repairs, high tension wounds, many orthopedic repairs and some types of surgical anastomoses.

Bioabsorbable sutures can be made of materials which are broken down in tissue after a given period of time, which depending on the material can be from ten days to eight weeks. The sutures are used therefore in many of the internal tissues of the body. In most cases, three weeks is sufficient for the wound to close firmly. At that time the suture is not needed any more, and the fact that it disappears is an advantage, as there is no foreign material left inside the body and no need for the patient to have the sutures removed. In rare cases, bioabsorbable sutures can cause inflammation and be rejected by the body rather than absorbed. Bioabsorbable sutures were first made from the intestines of mammals. For example, gut sutures can be made of specially prepared bovine or ovine intestine, and can be untreated (plain catgut), tanned with chromium salts to increase the suture persistence in the body (chromic catgut), or heat-treated to give more rapid absorption (fast catgut). Concern about transmitting diseases such as bovine spongiform encephalopathy, has resulted in the gut being harvested from stock which have been tested to determine that the natural polymers used as suture materials do not carry viral diseases. Bioabsorbable sutures can be made of synthetic polymer fibers, which can be monofilaments or braided.

Self-retaining sutures are designed for engaging tissue when the suture is pulled in a direction other than that in which it was originally deployed in the tissue. Knotless tissue-approximating devices having barbs have been previously described in, for example, U.S. Pat. No. 5,374,268, disclosing armed anchors having barb-like projections, while suture assemblies having barbed lateral members have been described in U.S. Pat. Nos. 5,584,859 and 6,264,675. One of the earlier patents describing a barbed suture is U.S. Pat. No. 3,716,058, which discloses a suture having one or more relatively rigid barbs at its opposite ends; the presence of the barbs just at the ends of the suture would limit the barbs' effectiveness. Sutures having a plurality of barbs positioned along a greater portion of the suture are described in U.S. Pat. No. 5,931,855, which discloses a unidirectional barbed suture, and U.S. Pat. No. 6,241,747, which discloses a bidirectional barbed suture. Methods and apparatus for forming barbs on sutures by cutting barbs into a suture body have been described in, for example, U.S. Pat. Nos. 6,848,152 and 7,225,512. Methods of manufacturing sutures with frustoconical retainers have also been described, for example, in European Patent 1 075 843 and U.S. Pat. Publication No. 2007/0038429.

Despite the advantages of existing self-retaining sutures, there still remains a need and desire for new and preferably improved self-retaining sutures, and method of making the same.

BRIEF SUMMARY OF INVENTION

Provided herein are sutures for use in a procedure applied to tissue, and methods for forming such sutures. In accordance with an embodiment, a suture includes an elongated suture body and plurality of retainers that are spaced apart from one another and extend from the elongated suture body between first and second ends of the suture body. In specific embodiments, the retainers are bi-directional retainers.

In accordance with an embodiment of the present invention, each bi-directional retainer is deployable through tissue in two directions generally opposite one another, but once deployed in one direction resists movement in the generally opposite direction. Advantageously, this allows the number of bi-directional retainers that are deployed in one direction and the number of bi-directional retainers that are deployed in the generally opposite direction to be decided during a surgical procedure, on-the-fly. Viewed in another way, how much of the suture is deployed through tissue in the one direction and how much of the suture is deployed through tissue in the another direction can be decided during a surgical procedure because the suture does not have a predetermined transition segment or point.

In accordance with an embodiment of the present invention, each bi-directional retainer can be collapsed in either of two directions, depending upon the direction in which the retainer is deployed through tissue. In accordance with an embodiment, each retainer collapses in a direction opposite to the direction in which the retainer is deployed through tissue. Once a retainer is collapsed due to the retainer being deployed through tissue in a first direction, the retainer will substantially yield to motion of the elongated suture body within the tissue when the elongated suture body is drawn in the first direction, and will resist motion of the elongated suture body in a second direction generally opposite the first direction.

In accordance with an embodiment of the present invention, a shape of each retainer can be transformed in either of two manners, depending upon the direction in which the retainer is deployed through tissue. Once a retainer is transformed in shape due to the retainer being deployed through tissue in a first direction, the retainer will substantially yield to motion of the elongated suture body within the tissue when the elongated suture body is drawn in the first direction, and will resist motion of the elongated suture body in a second direction generally opposite the first direction. Once a retainer is transformed in shape due to the retainer being deployed through tissue in the second direction, the retainer will substantially yield to motion of the elongated suture body within the tissue when the elongated suture body is drawn in the second direction, and will resist motion of the elongated suture body in the first direction.

In accordance with alternative embodiments of the present invention, a suture includes an elongated suture body and a plurality of conical shaped retainers spaced apart from one another and extending from the elongated suture body between first and second ends of the suture body. Additionally, tissue engaging protrusions extend from the edges of the conical shaped retainers and/or the angled walls of the conical shaped retainers.

The details of one or more embodiments are set forth in the description below. Other features, objects and advantages will be apparent from the description, the drawings, and the claims. In addition, the disclosures of all patents and patent applications referenced herein are incorporated by reference in their entirety.

The details of one or more aspects or embodiments are set forth in the description below. Other features, objects and advantages will be apparent from the description, the drawings, and the claims. In addition, the disclosures of all patents and patent applications referenced herein are incorporated by reference in their entirety.

DESCRIPTION OF INVENTION

Figure 1:
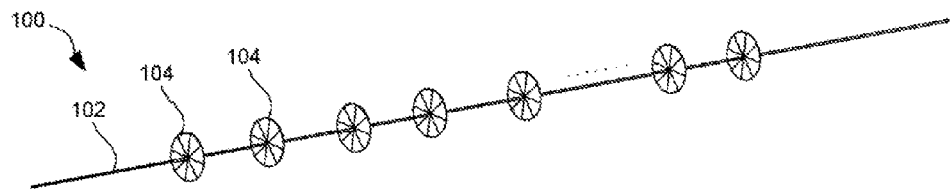
FIG. 1 is perspective view of a portion of a self-retaining suture according to an embodiment of the present invention, which includes bi-directional retainers.

Prior to setting forth the invention, it may be helpful to an understanding thereof to first set forth definitions of certain terms that are used hereinafter.

"Self-retaining system" refers to a self-retaining suture together with means for deploying the suture into tissue. Such deployment means include, without limitation, suture needles and other deployment devices as well as sufficiently rigid and sharp ends on the suture itself to penetrate tissue.

"Self-retaining suture" refers to a suture that does not require a knot or a suture anchor at its end in order to maintain its position into which it is deployed during a surgical procedure. These may be monofilament sutures or braided sutures, and are positioned in tissue in two stages, namely deployment and affixation, and include at least one tissue retainer.

"Tissue retainer" (or simply "retainer" or "barb") refers to a suture element having a retainer body projecting from the suture body and a retainer end adapted to penetrate tissue. Each retainer is adapted to resist movement of the suture in a direction other than the direction in which the suture is deployed into the tissue by the surgeon, by being oriented to substantially face the deployment direction. As the tissue-penetrating end of each retainer moving through tissue during deployment faces away from the deployment direction (the direction of the passage of the suture during deployment), the tissue retainers should not catch or grab tissue during this phase. Once the self-retaining suture has been deployed, a force exerted in another direction, often substantially opposite to the deployment direction, to affix the suture in position causes retainers to be displaced from their deployment positions of resting substantially along the suture body and causes retainer ends to penetrate into the tissue resulting in tissue being caught between the retainer and the suture body.

"Retainer configurations" refers to configurations of tissue retainers and can include features such as size, shape, surface characteristics, and so forth. These are sometimes also referred to as "barb configurations".

"Bidirectional suture" refers to a self-retaining suture having retainers oriented in one direction at one end and retainers oriented in the other direction at the other end. A bidirectional suture is typically armed with a needle at each end of the suture thread. Many bidirectional sutures have a transitional segment located between the two barb orientations.

"Transition segment" refers to a retainer-free (barb-free) portion of a bidirectional suture located between a first set of retainers (barbs) oriented in one direction and a second set of retainers (barbs) oriented in another direction.

"Suture thread" refers to the filamentary body component of the suture, and, for sutures requiring needle deployment, does not include the suture needle. The suture thread may be monofilamentary, or, multifilamentary.

"Monofilament suture" refers to a suture comprising a monofilamentary suture thread.

"Braided suture" refers to a suture comprising a multifilamentary suture thread. The filaments in such suture threads are typically braided, twisted, or woven together.

"Degradable (also referred to as "biodegradable" or "bioabsorbable") suture" refers to a suture which, after introduction into a tissue is broken down and absorbed by the body. Typically, the degradation process is at least partially performed in a biological system. "Degradation" refers to a chain scission process by which a polymer chain is cleaved into oligomers and monomers. Chain scission may occur through various mechanisms, including, for example, by chemical reaction (e.g., hydrolysis, oxidation/reduction, enzymatic mechanisms or a combination or these) or by a thermal or photolytic process. Polymer degradation may be characterized, for example, using gel permeation chromatography (GPC), which monitors the polymer molecular mass changes during erosion and breakdown. Degradable suture material may include polymers such as catgut, polyglycolic acid, lactic acid polymers, polyether-esters (e.g., copolymers of polyglycolide with polyglycols, polyglycolide with polyethers, polylactic acid with polyglycols or polylactic acid with polyethers), copolymers of glycolide and lactide, copolymers of trimethylene carbonate and glycolide with diethylene glycol (e.g., MAXON™, Tyco Healthcare Group), terpolymer composed of glycolide, trimethylene carbonate, and dioxanone (e.g., BIOSYN™ [glycolide (60%), trimethylene carbonate (26%), and dioxanone (14%)], Tyco Healthcare Group), copolymers of glycolide, caprolactone, trimethylene carbonate, and lactide (e.g., CAPROSYN™, Tyco Healthcare Group). These sutures can be in either a braided multifilament form or a monofilament form. The polymers used in the present invention can be linear polymers, branched polymers or multi-axial polymers. Examples of multi-axial polymers used in sutures are described in U.S. Patent Application Publication Nos. 20020161168, 20040024169, and 20040116620. Degradable sutures can also include dissolvable sutures made of a dissolvable polymer, such as a polyvinyl alcohol partly deacetylated polymer, but not limited thereto. Sutures made from degradable suture material lose tensile strength as the material degrades.

"Non-degradable (also referred to as "non-absorbable") suture" refers to a suture comprising material that is not degraded by chain scission such as chemical reaction processes (e.g., hydrolysis, oxidation/reduction, enzymatic mechanisms or a combination or these) or by a thermal or photolytic process. Non-degradable suture material includes polyamide (also known as nylon, such as nylon 6 and nylon 6.6), polyethylene terephthlate, polytetrafluoroethylene, polyether-ester (such as polybutylene or polyethylene terepthalate based copolymers with polyglycols or polyethers), polyurethane, metal alloys, metal (e.g., stainless steel wire), polypropylene, polyethelene, silk, and cotton. Sutures made of non-degradable suture material are suitable for applications in which the suture is meant to remain permanently or is meant to be physically removed from the body.

"Suture diameter" refers to the diameter of the body of the suture. It is to be understood that a variety of suture lengths may be used with the sutures described herein and that while the term "diameter" is often associated with a circular periphery, it is to be understood herein to indicate a cross-sectional dimension associated with a periphery of any shape. Suture sizing is based upon diameter. United States Pharmacopeia ("USP") designation of suture size runs from 0 to 7 in the larger range and 1-0 to 11-0 in the smaller range; in the smaller range, the higher the value preceding the hyphenated zero, the smaller the suture diameter. The actual diameter of a suture will depend on the suture material, so that, by way of example, a suture of size 5-0 and made of collagen will have a diameter of 0.15 mm, while sutures having the same USP size designation but made of a synthetic absorbable material or a non-absorbable material will each have a diameter of 0.1 mm. The selection of suture size for a particular purpose depends upon factors such as the nature of the tissue to be sutured and the importance of cosmetic concerns; while smaller sutures may be more easily manipulated through tight surgical sites and are associated with less scarring, the tensile strength of a suture manufactured from a given material tends to decrease with decreasing size. It is to be understood that the sutures and methods of manufacturing sutures disclosed herein are suited to a variety of diameters, including without limitation 7, 6, 5, 4, 3, 2, 1, 0, 1-0, 2-0, 3-0, 4-0, 5-0, 6-0, 7-0, 8-0, 9-0, 10-0 and 11-0.

"Suture deployment end" refers to an end of the suture to be deployed into tissue; one or both ends of the suture may be suture deployment ends. The suture deployment end may be attached to deployment means such as a suture needle, or may be sufficiently sharp and rigid to penetrate tissue on its own.

"Armed suture" refers to a suture having a suture needle on at least one suture deployment end.

"Needle attachment" refers to the attachment of a needle to a suture requiring same for deployment into tissue, and can include methods such as crimping, swaging, using adhesives, and so forth. The point of attachment of the suture to the needle is known as the swage.

"Suture needle" refers to needles used to deploy sutures into tissue, which come in many different shapes, forms and compositions. There are two main types of needles, traumatic needles and atraumatic needles. Traumatic needles have channels or drilled ends (that is, holes or eyes) and are supplied separate from the suture thread and are threaded on site. Atraumatic needles are eyeless and are attached to the suture at the factory by swaging whereby the suture material is inserted into a channel at the blunt end of the needle which is then deformed to a final shape to hold the suture and needle together. As such, atraumatic needles do not require extra time on site for threading and the suture end at the needle attachment site is smaller than the needle body. In the traumatic needle the thread comes out of the needle's hole on both sides and often the suture rips the tissues to a certain extent as it passes through. Most modern sutures are swaged atraumatic needles. Atraumatic needles may be permanently swaged to the suture or may be designed to come off the suture with a sharp straight tug. These "pop-offs" are commonly used for interrupted sutures, where each suture is only passed once and then tied. For barbed sutures that are uninterrupted, these atraumatic needles would be ideal.

Suture needles may also be classified according to their point geometry. For example, needles may be (i) "tapered" whereby the needle body is round and tapers smoothly to a point; (ii) "cutting" whereby the needle body is triangular and has sharpened cutting edge on the inside; (iii) "reverse cutting" whereby the cutting edge is on the outside; (iv) "trocar point" or "tapercut" whereby the needle body is round and tapered, but ends in a small triangular cutting point; (v) "blunt" points for sewing friable tissues; (vi) "side cutting" or "spatula points" whereby the needle is flat on top and bottom with a cutting edge along the front to one side (these are typically used for eye surgery).

Suture needles may also be of several shapes including, (i) straight, (ii) half curved or ski, (iii) ¼ circle, (iv) ⅜ circle, (v) ½ circle, (vi) ⅝ circle, (v) and compound curve.

Suturing needles are described, for example, in U.S. Pat. Nos. 6,322,581 and 6,214,030 (Mani, Inc., Japan); and 5,464,422 (W.L. Gore, Newark, Del.); and 5,941,899; 5,425,746; 5,306,288 and 5,156,615 (US Surgical Corp., Norwalk, Conn.); and 5,312,422 (Linvatec Corp., Largo, Fla.); and 7,063,716 (Tyco Healthcare, North Haven, Conn.). Other suturing needles are described, for example, in U.S. Pat. Nos. 6,129,741; 5,897,572; 5,676,675; and 5,693,072. The sutures described herein may be deployed with a variety of needle types (including without limitation curved, straight, long, short, micro, and so forth), needle cutting surfaces (including without limitation, cutting, tapered, and so forth), and needle attachment techniques (including without limitation, drilled end, crimped, and so forth). Moreover, the sutures described herein may themselves include sufficiently rigid and sharp ends so as to dispense with the requirement for deployment needles altogether.

"Needle diameter" refers to the diameter of a suture deployment needle at the widest point of that needle. While the term "diameter" is often associated with a circular periphery, it is to be understood herein to indicate a cross-sectional dimension associated with a periphery of any shape.

"Wound closure" refers to a surgical procedure for closing of a wound. An injury, especially one in which the skin or another external or internal surface is cut, torn, pierced, or otherwise broken is known as a wound. A wound commonly occurs when the integrity of any tissue is compromised (e.g., skin breaks or burns, muscle tears, or bone fractures). A wound may be caused by an act, such as a gunshot, fall, or surgical procedure; by an infectious disease; or by an underlying medical condition. Surgical wound closure facilitates the biological event of healing by joining, or closely approximating, the edges of those wounds where the tissue has been torn, cut, or otherwise separated. Surgical wound closure directly apposes or approximates the tissue layers, which serves to minimize the volume new tissue formation required to bridge the gap between the two edges of the wound. Closure can serve both functional and aesthetic purposes. These purposes include elimination of dead space by approximating the subcutaneous tissues, minimization of scar formation by careful epidermal alignment, and avoidance of a depressed scar by precise eversion of skin edges.

"Tissue elevation procedure" refers to a surgical procedure for repositioning tissue from a lower elevation to a higher elevation (i.e. moving the tissue in a direction opposite to the direction of gravity). The retaining ligaments of the face support facial soft tissue in the normal anatomic position. However, with age, gravitational effects achieve a downward pull on this tissue and the underlying ligaments, and fat descends into the plane between the superficial and deep facial fascia, thus allowing facial tissue to sag. Face-lift procedures are designed to lift these sagging tissues, and are one example of a more general class of medical procedure known as a tissue elevation procedure. More generally, a tissue elevation procedure reverses the appearance change that results from gravitation effects over time, and other temporal effects that cause tissue to sag, such as genetic effects. It should be noted that tissue can also be repositioned without elevation; in some procedures tissues are repositioned laterally (away from the midline), medially (towards the midline) or inferiorly (lowered) in order to restore symmetry (i.e. repositioned such that the left and right sides of the body "match").

"Medical device" or "implant" refers to any object placed in the body for the purpose of restoring physiological function, reducing/alleviating symptoms associated with disease, and/or repairing/replacing damaged or diseased organs and tissues. While normally composed of biologically compatible synthetic materials (e.g., medical-grade stainless steel, titanium and other metals: polymers such as polyurethane, silicon, PLA, PLGA and other materials) that are exogenous, some medical devices and implants include materials derived from animals (e.g., "xenografts" such as whole animal organs; animal tissues such as heart valves; naturally occurring or chemically-modified molecules such as collagen, hyaluronic acid, proteins, carbohydrates and others), human donors (e.g., "allografts" such as whole organs; tissues such as bone grafts, skin grafts and others), or from the patients themselves (e.g., "autografts" such as saphenous vein grafts, skin grafts, tendon/ligament/muscle transplants). Medical devices that can be used in procedures in conjunction with the present invention include, but are not restricted to, orthopaedic implants (artificial joints, ligaments and tendons; screws, plates, and other implantable hardware), dental implants, intravascular implants (arterial and venous vascular bypass grafts, hemodialysis access grafts; both autologous and synthetic), skin grafts (autologous, synthetic), tubes, drains, implantable tissue bulking agents, pumps, shunts, sealants, surgical meshes (e.g., hernia repair meshes, tissue scaffolds), fistula treatments, spinal implants (e.g., artificial intervertebral discs, spinal fusion devices, etc.) and the like.

A. Self-Retaining Sutures

Self-retaining sutures (including barbed sutures) differ from conventional sutures in that they possess numerous tissue retainers (such as barbs) which anchor into the tissue following deployment and resist movement of the suture in a direction opposite to that in which the retainers face, thereby eliminating the need to tie knots to affix adjacent tissues together (a "knotless" closure). By eliminating knot tying, associated complications are eliminated, including, but not limited to (i) spitting (a condition where the suture, usually a knot) pushes through the skin after a subcutaneous closure), (ii) infection (bacteria are often able to attach and grow in the spaces created by a knot), (iii) bulk/mass (a significant amount of suture material left in a wound is the portion that comprises the knot), (iv) slippage (knots can slip or come untied), and (v) irritation (knots serve as a bulk "foreign body" in a wound). Suture loops associated with knot tying may lead to ischemia (they create tension points that can strangulate tissue and limit blood flow to the region) and increased risk of dehiscence or rupture at the surgical wound. Knot tying is also labor intensive and can comprise a significant percentage of the time spent closing a surgical wound. Additional operative procedure time is not only bad for the patient (complication rates rise with time spent under anesthesia), but it also adds to the overall cost of the operation (many surgical procedures are estimated to cost between $15 and $30 per minute of operating time). Thus, knotless sutures not only allow patients to experience an improved clinical outcome, but they also save time and costs associated with extended surgeries and follow-up treatments.

Self-retaining systems for wound closure also result in better approximation of the wound edges, evenly distribute the tension along the length of the wound (reducing areas of tension that can break or lead to ischemia), decrease the bulk of suture material remaining in the wound (by eliminating knots) and reduce spitting (the extrusion of suture material—typically knots—through the surface of the skin. All of these features are thought to reduce scarring, improve cosmesis, and increase wound strength relative to wound closures effected with plain sutures or staples.

The ability of self-retaining sutures to anchor and hold tissues in place even in the absence of tension applied to the suture is a feature that also provides superiority over plain sutures. When closing a wound that is under tension, this advantage manifests itself in several ways: (i) a multiplicity of retainers can dissipate tension along the entire length of the suture (providing hundreds of "anchor" points as opposed to knotted interrupted sutures which concentrate the tension at discrete points; this produces a superior cosmetic result and lessens the chance that the suture will "slip" or pull through); (ii) complicated wound geometries can be closed (circles, arcs, jagged edges) in a uniform manner with more precision and accuracy than can be achieved with interrupted sutures; (iii) they eliminate the need for a "third hand" which is often required for maintaining tension across the wound during traditional suturing and knot tying (to prevent "slippage" when tension is momentarily released during tying); (iv) they are superior in procedures where knot tying is technically difficult, such as in deep wounds or laparoscopic procedures; and (v) they can be used to approximate and hold the wound prior to definitive closure. As a result, self-retaining sutures provide easier handling in anatomically tight or deep places (such as the pelvis, abdomen and thorax) and make it easier to approximate tissues in laparoscopic and minimally invasive procedures; all without having to secure the closure via a knot. Greater accuracy allows self-retaining sutures to be used for more complex closures (such as those with diameter mismatches, larger defects or purse string suturing) than can be accomplished with plain sutures.

Self-retaining sutures also lend themselves to a variety of specialized indications; for example, they are suitable for tissue elevation procedures where tissue is moved from its previous location and repositioned into a new anatomical location (this is typically performed in cosmetic procedures where "drooping" tissue is elevated and fixed in a more "youthful" position; or where "out-of-position" tissue is moved back to its correct anatomical location). Such procedures include facelifts, brow lifts, breast lifts, buttocks lifts, and so forth.

A self-retaining suture may be unidirectional, having one or more retainers oriented in one direction along the length of the suture thread; or bidirectional, typically having one or more retainers oriented in one direction along a portion of the thread, followed by one or more retainers oriented in another (often opposite) direction over the remainder of the thread (as described with barbed retainers in U.S. Pat. Nos. 5,931,855 and. 6,241,747).

Although any number of sequential or intermittent configurations of retainers are possible, a common form involves a needle at one end, followed by barbs projecting "away" from the needle until the transition point (often the midpoint) of the suture is reached; at the transition point the configuration of barbs reverses itself about 180° (such that the barbs are now facing in the opposite direction) along the remaining length of the suture thread before attaching to a second needle at the opposite end (with the result that the barbs on this portion of the suture also face away from the nearest needle). Put another way, the barbs on both "halves" of a bidirectional self-retaining suture point towards the middle, with a transition segment (lacking retainers) interspersed between them, and with a needle attached to either end.

Despite the multitude of advantages of self-retaining sutures, there remains a need and desire to improve upon the design of such sutures so that a variety of common limitations can be eliminated.

B. Bi-Directional Retainers

FIG. 1 shows a perspective view of a portion of a self-retaining suture 100, according to an embodiment of the present invention, that includes an elongated threadlike suture body 102 and a plurality of retainers 104 projecting from the suture body 102. The suture body 102 can include two ends, or more than two ends (e.g., three ends, four ends, or more). The self-retaining suture 100 shown in FIG. 1 has not yet been deployed through patient tissue.

As shown in FIG. 1, the retainers 104 can be generally flat prior to being deployed through tissue, e.g., during a surgical procedure. As also shown in FIG. 1, the retainers can be generally orthogonal to the suture body 102, prior to being deployed through tissue. The retainers 104 may be referred to as bi-directional retainers 104, because they can be deployed in two directions, but once deployed in one direction, resist motion in the opposite direction, as will be appreciated from the discussion below. Advantageously, this allows the number of bi-directional retainers 104 that are deployed in one direction and the number of bi-directional retainers 104 that are deployed in the opposite direction to be decided during a surgical procedure. More specifically, prior to being deployed through tissue, each bi-directional retainer 104 is deployable through tissue in both a first direction and a second direction generally opposite the first direction. However, once a bi-directional retainer 104 is deployed through tissue in one of the first and second directions, the bi-direction retainer 104 will substantially yield to motion of the elongated suture body 102 within the tissue when the elongated suture body 102 is drawn in the one of the first and second directions, and will resist motion of the elongated suture body 102 in the other one of the first and second directions.

Figure 2A:
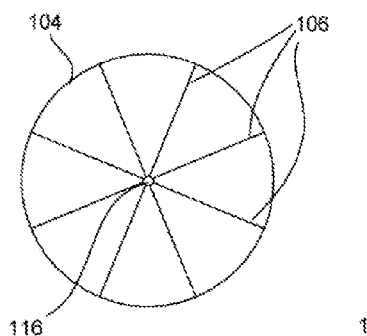
FIGS. 2A-2C are front views of the bi-directional retainers of FIG. 1, according to various embodiments of the present invention.
Figure 2B:
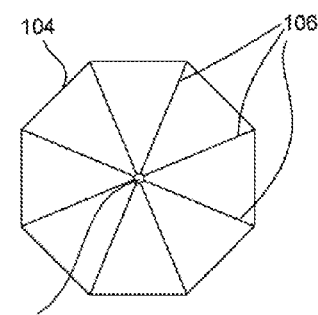
Figure 2C:
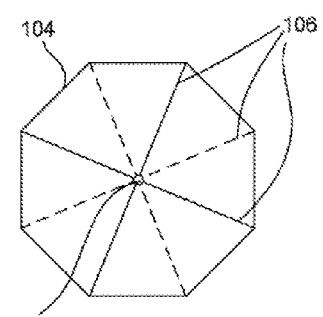

As can be seen from the front views in FIGS. 2A and 2B, the retainers 104 can be circular in shape (FIG. 2A), or can have other shapes such as but not limited to octagonal (FIG. 2B), hexagonal, square, and the like. Each retainer 104 include grooves 106 that extend radially from the center to the outer periphery or edge of the retainer. The grooves 106 can be continuous from the center to the outer edge, or can be discontinuous or intermittent (similar to how a perforation includes intermittent holes). The grooves 106 can cut into the retainers 104 (and thus be scores), or formed as part of a molding and/or heading process, e.g., at the same time the retainers 104 are formed. More or less grooves 106 than shown in FIGS. 2A-2C can be used. Also, as described below, each groove shown in FIGS. 2A-2C can be replaced with pairs of side-by-side grooves, or three or more side-by-side grooves.

Figure 3A:
FIGS. 3A-3H are cross sectional views of grooves in the bi-directional retainers of FIGS. 2A-2C, according to various embodiments of the present invention.
Figure 3B:
Figure 3C:
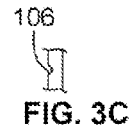
Figure 3D:
Figure 3E:
Figure 3F:
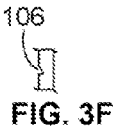
Figure 3G:
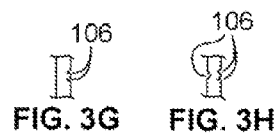
Figure 3H:
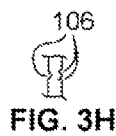

FIGS. 3A-3F, which illustrate alternative cross sectional portions of the retainers 104, show various embodiments of the grooves 106. Each retainer 104 has two generally planer sides, which can be referred to as first and second sides, left and right sides, or the like. As shown in FIGS. 3A and 3D, only one side of the retainer 104 can include grooves 106, or as shown in FIGS. 3C and 3F only the other side of the retainer 104 can include grooves 106. Alternatively, as shown in FIGS. 3B and 3E, both sides of the retainer 104 can include grooves 106. Where both sides of the retainer 104 includes grooves, the grooves 106 on one side can mirror the grooves on the other side. Alternatively, grooves 106 can be on both sides of the retainer 104 that do not mirror one another, as can be appreciated from FIG. 2C, where solid lines 106 represent grooves on one side, and dashed lines 106 represent grooves on the other side. Notice that the shape of the grooves 106 in FIGS. 3A-3C differ from the shape of the grooves 106 in FIGS. 3D-3F. A pair of grooves can be side-by-side, as shown in FIG. 3G, or three or more grooves can be side-by-side to form a sinusoidal wave of grooves, as shown in FIG. 3H. It specific embodiments, the grooves can have uniform thickness and/or depth. In other embodiments, the grooves can have varying thickness and/or depth, e.g. to allow for greater deformation near the center of each retainer 104. For a more specific example, each groove can have a greatest thickness and/or depth near the center or opening 116 of the retainer, and be narrowest and/or shallowest at the outer edge of the retainer. While in FIGS. 3A-3H the grooves 106 are shown as being generally triangular in shape, other shapes are also possible, such as, but not limited to square shaped, U-shaped, and the like.

Figures 4A, 4B, 4C:
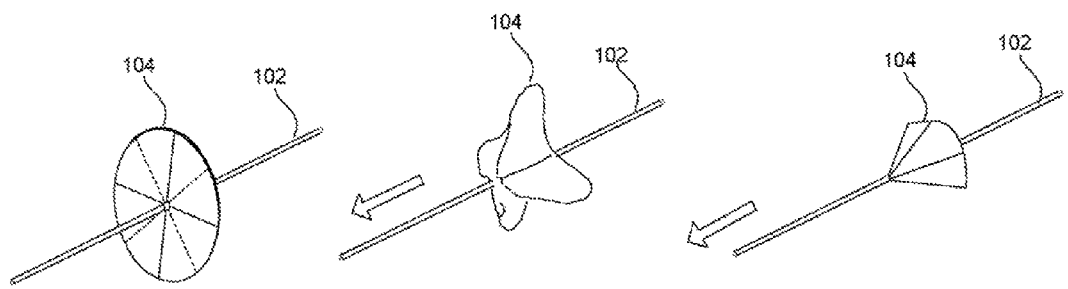
FIG. 4A is a perspective view of a portion of the self-retaining suture of FIG. 1, prior to it being deployed through patient tissue.
FIG. 4B is a perspective view of the self-retaining suture of FIG. 1 (and FIG. 4A), when it is initially being deployed through patient tissue.
FIG. 4C is a perspective view of the self-retaining suture of FIG. 1 (and FIGS. 4A and 4B) after it has been deployed through patient tissue.

As can be appreciated from FIGS. 1 and 4A, the sides of the retainers 104 are initially generally perpendicular to the suture body 102. This also means that the grooves 106 are initially generally perpendicular to the suture body 102. However, once the suture is used in a surgical procedure, and threaded through patient tissue, the resistance provided by the patient tissue will cause the retainers 104 to collapse, as can be appreciated from FIGS. 4B and 4C. FIG. 4B shows the retainer 104 as it initially begins to collapse. FIG. 4C shows the retainer 104 after it has been collapsed, i.e., in its collapsed position. The grooves 106 act as fold or collapse lines, so that the retainer 104 collapses in a controlled manner. The collapse occurs in a somewhat accordion fashion in that the folding along the grooves 106 alternates back and forth.

Each retainer 104 can be collapsed in either of two directions, depending upon the direction in which the retainer is deployed through tissue. The retainer 104 can collapse in the direction of the grooves, but may also collapse in the direction opposite of the grooves. In other words, if the grooves are on the right side of the retainer 104, and the suture body 102 with the retainer is pulled through tissue (i.e., deployed) in a leftwardly direction, the retainer 104 will collapse rightwardly, as shown in FIGS. 4B and 4C. However, if the same suture body 102 is initially pulled through tissue (i.e., deployed) in a rightwardly direction, the retainer 104 will collapse leftwardly, even though the grooves are only on the right side of the retainer 104. In other words, each retainer 104 collapses in a direction opposite to the direction in which the retainer is deployed through tissue.

Once in the collapsed position (e.g., as shown in FIG. 4C), the retainer 104 substantially yields to motion of the elongated suture body 102 within the tissue when the suture 100 is drawn in the suture deployment direction that caused the retainer to collapse, and resists motion if the suture 100 is drawn in a direction opposite the suture deployment direction. For example, it can be appreciated from FIG. 4C that the collapsed retainer 104 can be readily pulled through tissue in the direction of the arrow, but would resist motion in a direction opposite the arrow. Stated more generally, once a bi-directional retainer 104 is collapsed due to the retainer being deployed through tissue in a first direction, that retainer 104 will substantially yield to motion of the elongated suture body 102 within the tissue when the elongated suture body 102 is drawn in the first direction, and will resist motion of the elongated suture body 102 in a second direction generally opposite the first direction. More generally, each bi-directional retainer 104 can be deployed in either of two directions, and once deployed, yields to motion in the direction in which the retainer was deployed through tissue, and resists motion in the direction opposite the deployment direction.

Self-retaining sutures 100 that include the bi-directional retainers 104 can be used unidirectionally or bidirectionally. If intended to be used unidirectionally, the self-retaining sutures can include an end that is pointed or has a needle to allow penetration and passage through tissue when drawn by the end and an opposite end that includes in some embodiments an anchor for engaging tissue at the initial insertion point to limit movement of the suture. If intended to be used bi-directionally, more than one end of the suture can include a point or needle for tissue penetration. In other words, a bidirectional suture can be armed with a needle at each end of the suture thread.

Conventionally, a bi-directional self-retaining suture include a group of retainers extending toward one deployment direction along one portion of the suture and opposing retainers grouped and extending toward an opposing deployment direction along another portion of the suture. Also, conventionally a bi-directional self-retaining suture includes a transitional segment located between the two groups of retainers. A problem with such conventional bi-directional self-retaining sutures is that a surgeon needs to be cognizant of the location of the transitional segment when deploying the suture. Further, if the transitional segment is in the middle of the suture, the suture length on one side of the transitional segment may be shorter than is desired by the surgeon in some instances.

Additionally, the marking of the transition point of conventional bi-directional self retaining sutures is not always satisfactory. A drawback of current bi-directional self retaining sutures is that there are additional manufacturing and technical hurdles to achieve effective marking of the transition point. Further, a transition point may not always be at a location desired by certain doctors and/or appropriate or optimal for certain procedures.

Figure 5:
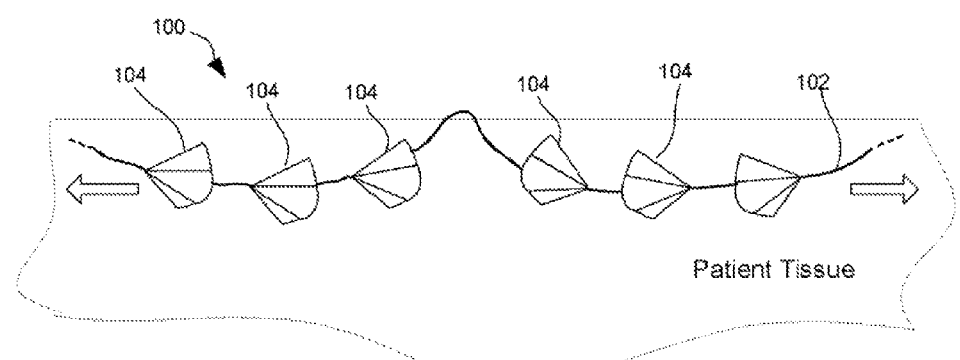
FIG. 5 illustrates that the bi-directional retainers of FIGS. 1-4C can be deployed through patient tissue in different directions.

Bi-directional self-retaining sutures 100 that include the bi-directional retainers 104 overcome the aforementioned deficiencies of conventional bi-directional self-retaining sutures. This is because bi-directional self-retaining sutures 100 that include the bi-directional retainers 104 can be deployed in either direction, but once deployed, resist movement in the direction opposite to the deployment rejection. For example, if a suture includes N spaced apart retainers 104, any where from all to none (i.e., M, where 0≤M≤N) of the retainers 104 can be collapsed in one direction by drawing all or part of the suture through patient tissue in a first direction, while the remaining retainers 104 (i.e., N-M) can be collapsed in the opposite direction by drawing the remaining portion of the suture through patient tissue in a second direction. Thereafter, i.e., once collapsed, each of the retainers 104 will resist movement in the direction opposite to its deployment direction. For example, M retainers 104 can resist movement in a first direction, and N-M retainers 104 can resist movement in a second direction opposite the first direction, where the variable M can be selected on-the-fly. Stated another way, the number of bi-directional retainers 104 that are deployed in one direction and the number of bi-directional retainers 104 that are deployed in the opposite direction can be decided during a surgical procedure. This can be appreciated from the illustration in FIG. 5. Further, unlike conventional bi-directional self-retaining sutures where a transitional segment is typically included between two groups of retainers that are deployable in opposite directions, with the bi-directional self-retaining sutures 100 that include the bi-directional retainers 104 a transitional segment need not be included. Additionally, the same bi-directional self-retaining suture 100 that includes the bi-directional retainers 104 can be efficiently and effectively used regardless of the desired and/or optimal transition point. Additionally, if the suture includes a needle at two ends of the suture body, a doctor can change the transition point at any time during a procedure. For example, the doctor can stitch with one needle and then when he is done, no matter how much of the suture has been used so far, the doctor can then start stitching with the other needle for the rest of the suture. This is beneficial over a suture having a fixed symmetrical or asymmetrical transition segment, because the transition segment can be anywhere the doctor selects for any procedure and at anytime time during the procedure.

Figure 6A:
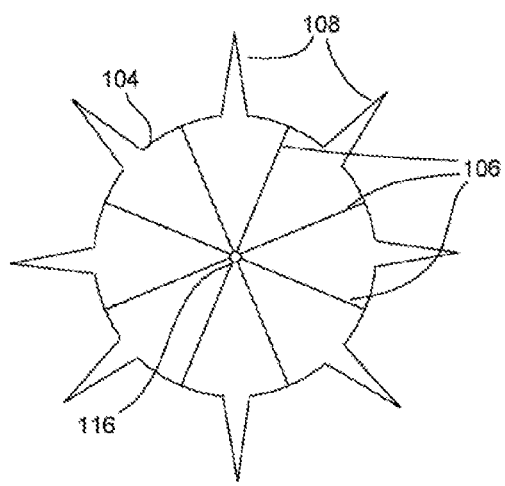
FIGS. 6A and 6B are front views of the bi-directional retainers that include protrusions extending from edges of the retainers, in accordance with embodiments of the present invention.
Figure 6B:
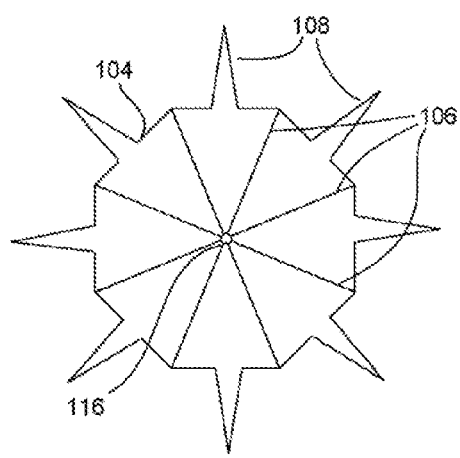
Figure 6C:
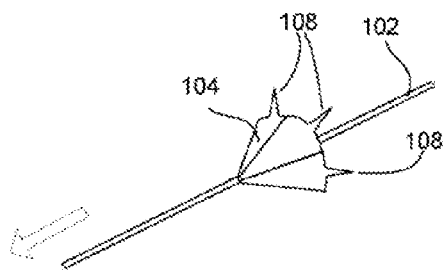
FIG. 6C is a perspective view of a suture that includes one of the bi-directional retainers of FIGS. 6A and 6B, after the retainer has been deployed through patient tissue.
Figure 6D:
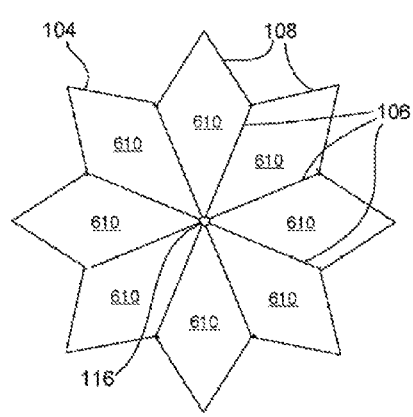
FIGS. 6D and 6E are front views of the bi-directional retainers that include protrusions extending from edges of the retainers, in accordance with further embodiments of the present invention where the protrusions are corners of quadrilateral faces.
Figure 6E:
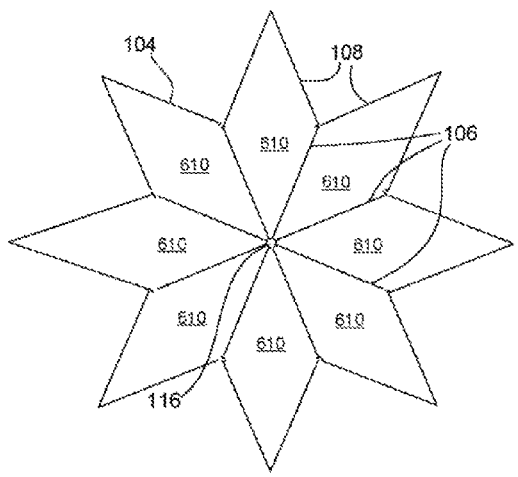

FIGS. 6A and 6B illustrate that the retainers 104 can include protrusions 108 along the outer edge of the retainers. The protrusions 108 provide for increased engagement of the retainers 104 with tissue. FIG. 6C illustrates one of the retainers 104 of FIG. 6A after it has been deployed through tissue and collapsed. It can be appreciated from FIG. 6C that if the suture body 102 were pulled in a direction opposite the arrow, the protrusions would stick into patient tissue, providing for even further resistance to movement in the direction opposite the arrow. As shown in FIGS. 6D and 6E, the protrusions 108 can be portions of quadrilateral faces 610. The quadrilateral faces 610 can be perfect rhomboids, as shown in FIG. 6E. By varying the dimension of each quadrilateral (and possibly rhomboidal) face 610, different final geometries can be achieved.

Figure 7:
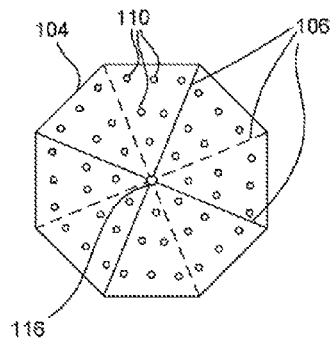
FIG. 7 is a front view of a bi-directional retainer that includes vents that prevent air from getting trapped by the retainer.

FIG. 7 illustrates that the retainers 104 can includes one or more vents 110 that prevent air from getting trapped by the retainers 104 as the retainers are deployed through patient tissue. This is advantageous, because it is believed that tissue will heal more quickly if there is no trapped air behind the retainer 104. Further, the vents provide for further anchoring of patient tissue.

The retainers 104 can be preformed and thereafter attached to the suture body 102. In an embodiment, each of the bi-directional retainers 104 includes an opening 116 therethrough. The suture body 102 can be threaded through the openings 116 of the retainers 104, and the retainers 104 can be attached to the suture body 102 such that the retainers 104 are spaced apart from one another. In an embodiment, the retainers 104 can be attached to the suture body 102 using an adhesive. Exemplary adhesives that can be used include, but are not limited to, cyanoacrylates (e.g., octylcyanoacrylate), fibrin sealants, gelatin glue, synthetic N-hydroxysuccinimide based adhesives and acrylic adhesives. Alternatively, externally activated adhesives can be used, such as materials from the polymerizable groups, such as acrylic and methacrylic functionalities, acrylamide, methacrylamide, itaconate and styrene groups, which will exhibit an adhesive quality upon exposure to high-frequency radiation (e.g., ultraviolet light or other high-frequency waves). Other adhesives which can be used include permanent silicone room temperature vulcanizing adhesives, free radical generating adhesives such as benzoyl peroxide and the like. In other embodiments, the retainers 104 are attached to the suture body 102 by melting the retainers 104 to the suture body 102. In other words, the retainers can be heat-bonded to the suture body 102. In some embodiments, the retainers 104 are attached to the suture body 102 by fusing the retainers 104 to the suture body 102 using welding, such as, but not limited to, ultrasonic welding or laser welding. In other words, the retainers 104 can be weld-bonded to the suture body 102. Alternatively, the retainers 104 are attached to the suture body 102 using a solvent, e.g., by partly or completely dissolving a portion of the retainers 104 into the suture body 102 and/or vice versa. In other words, the retainers can be solvent-bonded to the suture body 102.

Alternatively, the retainers 104 can be formed as an integral portion of (i.e., as a one piece structure with) the suture body 102, e.g., using extrusion, molding and/or heading processes. FIGS. 8, 9 and 10A-10C will be used to explain an exemplary process that can be used to produce the self retaining suture 100 include bi-directional retainers 104.

Figure 8:
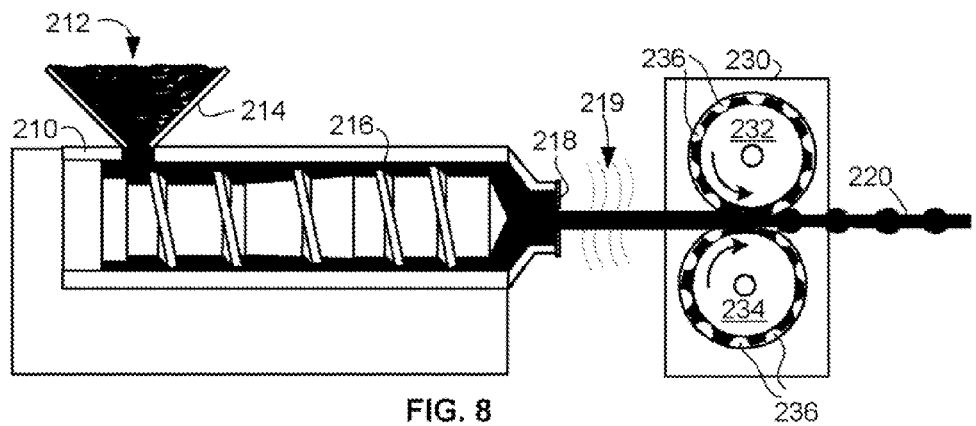
FIG. 8 illustrates an exemplary extruding and coining machine that can be used to produce the sutures described with reference to FIGS. 1-7, in accordance with an embodiment of the present invention.

Referring to FIG. 8, a monofilament 220 can be formed by extrusion and coining As shown in FIG. 8, an extruder 210 receives pellets of polymer 212 in hopper 214. The polymer is melted and pushed by screw 216 through extrusion die 218 to form filament 220 of melted polymer 212. The filament 220 initially has a uniform cross-section in the shape of the hole in the extrusion die 218. The extruded filament passes through an air gap 219 where the filament cools and polymer 212 solidifies somewhat. The extruded filament 220 is passed to coining machine 230 where filament 220 passes between two rollers 232, 234. The filament may optionally be quenched, drawn and/or tempered before and/or after the coining process. Rollers 232, 234 have a patterned surface which presses the material of filament 220 into the desired shape shown in FIG. 9. This coining process can be conducted at a temperature that is between 20-80% of the melting point of the polymer. In preferred embodiments, the coining process is conducted at temperatures above the glass transition temperature of the polymer and below the onset of melting temperature. In the configuration illustrated in FIG. 8, each of rollers 232, 234 has hemispherical indentations 236 on its outer surface such that as filament 220 passes through the rollers it takes on the shape shown in FIG. 9.

Figure 9:
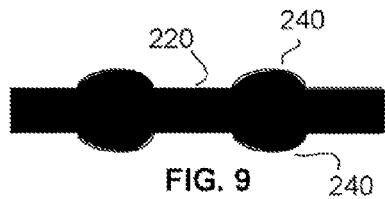
FIG. 9 illustrates an exemplary filament that can be produced using the machine of FIG. 8.
Figure 10A:
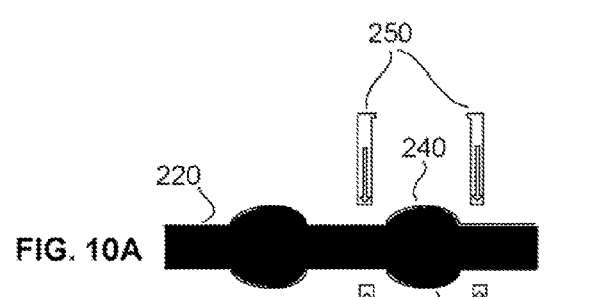
FIGS. 10A-10C illustrates how a mold or die can be used to produce the sutures described with reference to FIGS. 1-7 from the filament shown in FIG. 9.
Figure 10B:
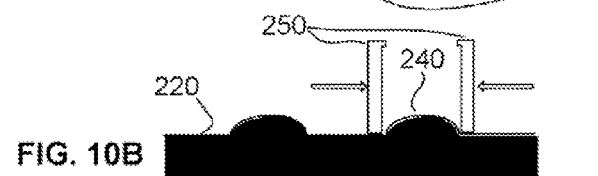
Figure 10C:
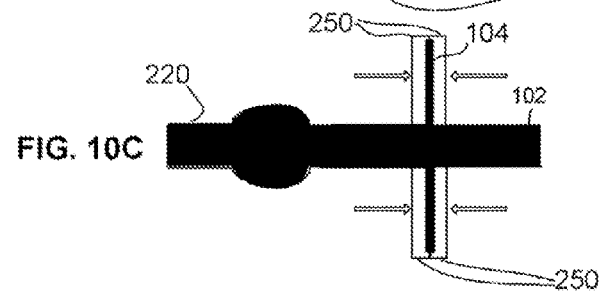

As shown in FIG. 9, the resulting filament 220 has intermittent hemispherical nodules 230. As can be appreciated from FIGS. 10A-10C, a mold or die 250 can be used in a molding and/or heading process to shape, coin or otherwise produce the bi-directional retainers 104 described above with reference to FIG. 1-7. The grooves 106 in the retainers 104 can be generated using the mold or die 250, or cut or machined into the retainers 104 thereafter, e.g., using a blade or the like.

FIGS. 2A, 2B, 6A and 6B discussed above illustrate alternative shapes for the bi-directional retainers 104. These are just a few possible shapes for the bi-direction retainers 104, which are not meant to be limiting. In other words, other shaped bi-directional retainers 104 are possible, and within the scope of the present invention.

The self-retaining suture 100 can include bi-directional retainers 104 of different sizes, which are designed for various surgical applications. For example, different retainers 104 can have different diameters. Relatively larger retainers are desirable for joining fat and soft tissues, whereas relatively smaller retainers are desirable for joining fibrous tissues. Use of a combination of large, medium, and/or small retainers on the same suture helps to ensure maximum anchoring properties when retainers sizes are customized for each tissue layer. The periodicity of the retainers 104 can be random or organized. The order of occurrence and the size of the groups may be altered to maximize tissue engagement strength.

The retainers 104 can be made of the same material as the suture body 102, or of a different material. In specific embodiments, the retainers 104 are made of a material that has a higher elastic constant (and thus stiffer) and/or a larger plastic zone (and thus more permanently deformable) than the material from which the suture body 102 is made. Also, the suture body 102 can be made of a material that is more flexible and/or more elastic than the material from which the retainers 104 are made. Furthermore the retainers 104 can have a greater toughness than the suture body to withstand the excess bending forces applied to them. Alternatively, the retainers 104 and the suture body 102 can be made of the same type of material, but the retainers when formed can be treated to increase their stiffness and strength, e.g., by appropriate annealing cycles (heating to a certain temperature and cooling at a certain rate) of the retainers 104, e.g., using techniques similar to those taught in U.S. Pat. No. 5,007,922, which is incorporated herein by reference.

The retainers 104 and the suture body 102 can both be made of bio-absorbable material, examples of which were provided above. Alternatively, the retainers 104 and the suture body 102 can both be made of non-absorbable material, examples of which were provided above. In still other embodiments, the retainers 104 can be bio-absorbable, while the suture body 102 is non-absorbable, or vice versa. In another embodiment of this invention the retainers 104 and/or the suture body 102 can be partially bio-absorbable, or a number of the retainers 104 can be bioabsorbable while the remaining retainers 104 are not bio-absorbable. Additionally, the suture body 102 can be made of a material having a greater tensile strength than the material used to make the retainers 104, or vice versa.

C. Uni-Directional Retainers

Figure 11A:
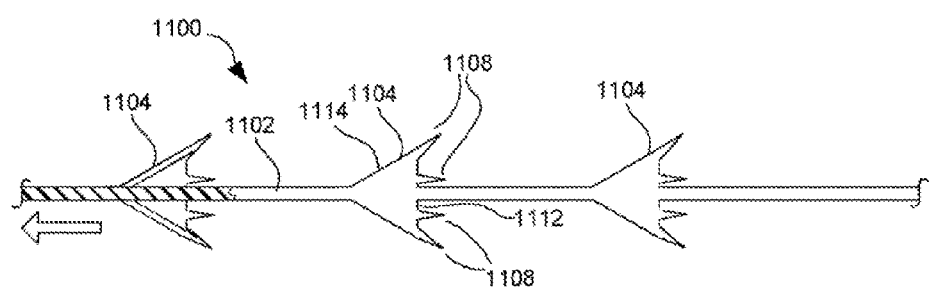
FIG. 11A illustrates a self-retaining suture that includes uni-directional retainers, according to an embodiment of the present invention.

Protrusions similar to protrusions 108 can also be provided on uni-directional retainers, as shown in FIGS. 11A-11E. In FIG. 11A, a self-retaining suture 1100 includes retainers 1104 that have a conical shape and include protrusions 1108. In FIGS. 11A-11D, the protrusions 1108 extend from ends 1112 of the main body of the conical retainer 1104. The retainers 1104 yield to motion of the elongated suture body within the tissue when the suture is drawn in the suture deployment direction represented by the arrow, and resists motion if the suture is drawn in a direction opposite the suture deployment direction (a direction opposite the arrow). If the suture 1100 were pulled in a direction opposite the arrow, the protrusions 1108 would stick into patient tissue, providing for even further resistance to movement in the direction opposite the arrow.

Figure 11B:
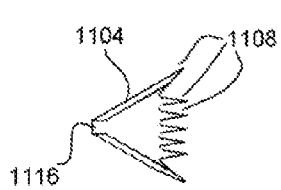
FIGS. 11B-11E illustrate alternative retainer embodiments for the self-retaining suture of FIG. 11A.
Figure 11C:
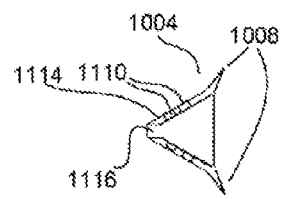
Figure 11D:
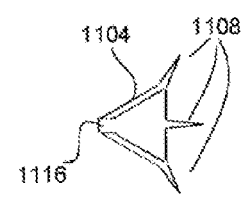
Figure 11E:
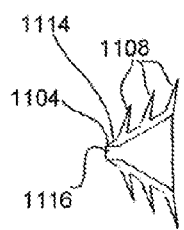

FIGS. 11B-11E illustrate some variations on retainer 1104. The retainer 1104 of FIG. 11B is similar to the retainer 1104 of FIG. 8, but includes a greater number of protrusions 1108. FIG. 11C illustrates that an angle of the protrusions 1108 of the retainers 1104 can be different (e.g., more or less obtuse) than the angle of the wall 1114 of the conical main body of the retainer 1104. The retainer 1104 of FIG. 11D is similar to the retainer 1104 of FIG. 11C, but includes a greater number of protrusions 1108. FIG. 11C also illustrates that the retainer 1104 can includes one or more vents 1110 in the angled walls 1114, where the vents prevent air from getting trapped by the retainers 1104 as the retainers are employed through patient tissue. This is advantageous, because it is believed that tissue will heal more quickly if there is no trapped air behind the retainer 1104. Further, the vents provide for further anchoring of the tissue. Such vents 1110 can be included in any of the retainers 1104 of FIGS. 11A-11E. Venting can also be provided by forming conical retainers from a mesh, perforated or porous material. The retainer 1104 of FIG. 11E includes protrusions 1108 that have a pointed end and extend from the angled wall 1114 of the conical main body of the retainer 1104. In each embodiment, the retainers 1104 yield to motion of the elongated suture body within the tissue when the suture is drawn in a first suture deployment direction, and resists motion if the suture is drawn in a direction opposite the suture deployment direction. When the retainers 1104 are pulled in a direction opposite their deployment direction, the pointed end of the protrusions 1108 will stick into patient tissue, providing for even further resistance to movement in the direction opposite the deployment direction.

While the conical retainers 1104 can have a circular cross section, the cross section may alternatively be elliptical, or some other shape. Also, it is noted that the instead of the angled walls 1114 being curved, it's possible that they are faceted. Further, the term conical is meant to encompass frusto-conical.

The retainers 1104 can be preformed and thereafter attached to a suture body 1102. In an embodiment, each of the retainers 1104 includes an opening 1116 therethrough. The suture body 1102 can be threaded through the openings 1116 of the retainers 1104, and the retainers 1104 can be attached to the suture body 1102 such that the retainers 104 are spaced apart from one another. The retainers can be attached to the suture body 1102 using an adhesive, by heat-bonding, by weld-bonding, by solvent-bonding, etc. Alternatively, the retainers 1104 can be formed as an integral portion of (i.e., as a one piece structure with) the suture body 1102, e.g., using extrusion, molding, machining and/or heading processes, e.g., in a manner similar to that described above with reference to FIGS. 8-10C.

The walls of the retainers 1104 are angled such that the retainers substantially yield to motion of the elongated suture body within the tissue when the suture is drawn in one suture deployment direction and resist motion if the suture is drawn in an opposite suture deployment direction. The self-retaining sutures 1100 can be unidirectional or bidirectional. If unidirectional sutures, the self-retaining sutures can include an end that is pointed or has a needle to allow penetration and passage through tissue when drawn by the end and an opposite end that includes in some embodiments an anchor for engaging tissue at the initial insertion point to limit movement of the suture. If bi-directional, the self-retaining sutures 1100 can include retainers 1104 grouped and extending toward one deployment direction along one portion of the suture and opposing retainers 1104 grouped and extending toward an opposing deployment direction along another portion of the suture. Accordingly, when such a bidirectional suture is implanted, both groups of retainers are engaging tissue, and the retainers can resist movement of the suture through tissue in either direction. Also, a bidirectional suture can be armed with a needle at each end of the suture thread. A bidirectional suture can also have a transitional segment located between the two groups of retainers.

The self-retaining suture 1100 of can include retainers 1104 of different sizes, which are designed for various surgical applications. For example, different retainers 1104 can have different cross-sectional diameters. Relatively larger retainers are desirable for joining fat and soft tissues, whereas relatively smaller retainers are desirable for joining fibrous tissues. Use of a combination of large, medium, and/or small retainers on the same suture helps to ensure maximum anchoring properties when retainers sizes are customized for each tissue layer. The periodicity of the retainers 104 can be random or organized. The order of occurrence and the size of the groups may be altered to maximize tissue engagement strength.

The retainers 1104 can be made of the same material as the suture body 1102, or of a different material. In specific embodiments, the retainers 1104 are made of a material that has a higher elastic constant (and thus stiffer) and/or a larger plastic zone (and thus more permanently deformable) than the material from which the suture body 1102 is made. Also, the suture body 1102 can be made of a material that is more flexible and/or more elastic than the material from which the retainers 1104 are made. Furthermore the retainers 1104 can have a greater toughness than the suture body to withstand the excess bending forces applied to them. Alternatively, the retainers 1104 and the suture body 1102 can be made of the same type of material, but the retainers when formed can be treated to increase their stiffness and strength, e.g., by appropriate annealing cycles (heating to a certain temperature and cooling at a certain rate) of the retainers 1104, e.g., using techniques similar to those taught in U.S. Pat. No. 5,007,922, which is incorporated herein by reference.

The retainers 1104 and the suture body 1102 can both be made of bio-absorbable material, examples of which were provided above. Alternatively, the retainers 1104 and the suture body 1102 can both be made of non-absorbable material, examples of which were provided above. In still other embodiments, the retainers 1104 can be bio-absorbable, while the suture body 1102 is non-absorbable, or vice versa. In another embodiment of this invention the retainers 1104 and/or the suture body 1102 can be partially bio-absorbable, or a number of the retainers 1104 can be bioabsorbable while the remaining retainers 1104 are not bio-absorbable. Additionally, the suture body 1102 can be made of a material having a greater tensile strength than the material used to make the retainers 1104, or vice versa.

D. Materials for Manufacture of Self-Retaining Sutures

The suture bodies and retainers described above can be made of any suitable biocompatible material, and may be further treated with any suitable biocompatible material, whether to enhance the sutures' strength, resilience, longevity, or other qualities, or to equip the sutures to fulfill additional functions besides joining tissues together, repositioning tissues, or attaching foreign elements to tissues.

The retainers described above may also incorporate materials that further promote tissue engagement. For example, forming the retainers of tissue engagement-promoting materials can enhance the ability of the sutures to stay in place. One such class of tissue engagement-promoting materials are porous polymers that can be extruded to form suture bodies, including both microporous polymers and polymers that can be extruded with bubbles (whether bioabsorbable or nonbioabsorbable). Retainers synthesized with such materials can have a three-dimensional lattice structure that increases tissue engagement surface area and permits tissue infiltration into the suture body itself, thus having a primary structure that promotes successful suture use. Moreover, by optimizing pore size, fibroblast ingrowth can be encouraged, further facilitating anchoring of the retainers in the tissue. Alternatively pro-fibrotic coatings or agents may be used to promote more fibrous tissue encapsulation of the retainers and therefore better engagement. Exemplary profibrotic materials, which can be used to form retainers 204 and/or which can be applied to retainers, to promote tissue growth, are disclosed in U.S. Pat. No. 7,166,570, entitled "Medical implants and fibrosis-inducing agents," which is incorporated herein by reference.

One such microporous polymer is ePTFE (expanded polytetrafluoroethylene). Self-retaining sutures incorporating ePTFE (and related microporous materials) are well-suited to uses requiring a strong and permanent lift (such as breast lifts, face lifts, and other tissue repositioning procedures), as tissue infiltration of the suture results in improved fixation and engraftment of the suture and the surrounding tissue thus providing superior hold and greater longevity of the lift.

Additionally, self-retaining sutures described herein may be provided with compositions to promote healing and prevent undesirable effects such as scar formation, infection, pain, and so forth. This can be accomplished in a variety of manners, including for example: (a) by directly affixing to the suture a formulation (e.g., by either spraying the suture with a polymer/drug film, or by dipping the suture into a polymer/drug solution), (b) by coating the suture with a substance such as a hydrogel which will in turn absorb the composition, (c) by interweaving formulation-coated thread (or the polymer itself formed into a thread) into the suture structure in the case of multi-filamentary sutures, (d) by inserting the suture into a sleeve or mesh which is comprised of, or coated with, a formulation, or (e) constructing the suture itself with a composition. Such compositions may include without limitation anti-proliferative agents, anti-angiogenic agents, anti-infective agents, fibrosis-inducing agents, anti-scarring agents, lubricious agents, echogenic agents, anti-inflammatory agents, cell cycle inhibitors, analgesics, and anti-microtubule agents. For example, a composition can be applied to the suture before the retainers are formed, so that when the retainers engage, the engaging surface is substantially free of the coating. In this way, tissue being sutured contacts a coated surface of the suture as the suture is introduced, but when the retainer engages, a non-coated surface of the retainer contacts the tissue. Alternatively, the suture may be coated after or during formation of retainers on the suture if, for example, a fully-coated rather than selectively-coated suture is desired. In yet another alternative, a suture may be selectively coated either during or after formation of retainers by exposing only selected portions of the suture to the coating. The particular purpose to which the suture is to be put or the composition may determine whether a fully-coated or selectively-coated suture is appropriate; for example, with lubricious coatings, it may be desirable to selectively coat the suture, leaving, for instance, the tissue-engaging surfaces of the sutures uncoated in order to prevent the tissue engagement function of those surfaces from being impaired. On the other hand, coatings such as those comprising such compounds as anti-infective agents may suitably be applied to the entire suture, while coatings such as those comprising fibrosing agents may suitably be applied to all or part of the suture (such as the tissue-engaging surfaces). The purpose of the suture may also determine the sort of coating that is applied to the suture; for example, self-retaining sutures having anti-proliferative coatings may be used in closing tumour excision sites, while self-retaining sutures with fibrosing coatings may be used in tissue repositioning procedures and those having anti-scarring coatings may be used for wound closure on the skin. As well, the structure of the suture may influence the choice and extent of coating; for example, sutures having an expanded segment may include a fibrosis-inducing composition on the expanded segment to further secure the segment in position in the tissue. Coatings may also include a plurality of compositions either together or on different portions of the suture, where the multiple compositions can be selected either for different purposes (such as combinations of analgesics, anti-infective and anti-scarring agents) or for their synergistic effects.

E. Clinical Uses

In addition to the general wound closure and soft tissue repair applications described in the preceding sections, self-retaining sutures can be used in a variety of other indications.

Self-retaining sutures described herein may be used in various dental procedures, i.e., oral and maxillofacial surgical procedures and thus may be referred to as "self-retaining dental sutures." The above-mentioned procedures include, but are not limited to, oral surgery (e.g., removal of impacted or broken teeth), surgery to provide bone augmentation, surgery to repair dentofacial deformities, repair following trauma (e.g., facial bone fractures and injuries), surgical treatment of odontogenic and non-odontogenic tumors, reconstructive surgeries, repair of cleft lip or cleft palate, congenital craniofacial deformities, and esthetic facial surgery. Self-retaining dental sutures may be degradable or non-degradable, and may typically range in size from USP 2-0 to USP 6-0.

Self-retaining sutures described herein may also be used in tissue repositioning surgical procedures and thus may be referred to as "self-retaining tissue repositioning sutures". Such surgical procedures include, without limitation, face lifts, neck lifts, brow lifts, thigh lifts, and breast lifts. Self-retaining sutures used in tissue repositioning procedures may vary depending on the tissue being repositioned; for example, sutures with larger and further spaced-apart retainers may be suitably employed with relatively soft tissues such as fatty tissues.

Self-retaining sutures described herein may also be used in microsurgical procedures that are performed under a surgical microscope (and thus may be referred to as "self-retaining microsutures"). Such surgical procedures include, but are not limited to, reattachment and repair of peripheral nerves, spinal microsurgery, microsurgery of the hand, various plastic microsurgical procedures (e.g., facial reconstruction), microsurgery of the male or female reproductive systems, and various types of reconstructive microsurgery. Microsurgical reconstruction is used for complex reconstructive surgery problems when other options such as primary closure, healing by secondary intention, skin grafting, local flap transfer, and distant flap transfer are not adequate. Self-retaining microsutures have a very small caliber, often as small as USP 9-0 or USP 10-0, and may have an attached needle of corresponding size. They may be degradable or non-degradable.

Self-retaining sutures as described herein may be used in similarly small caliber ranges for ophthalmic surgical procedures and thus may be referred to as "ophthalmic self-retaining sutures". Such procedures include but are not limited to keratoplasty, cataract, and vitreous retinal microsurgical procedures. Ophthalmic self-retaining sutures may be degradable or non-degradable, and have an attached needle of correspondingly-small caliber.

Self-retaining sutures can be used in a variety of veterinary applications for a wide number of surgical and traumatic purposes in animal health.

Although the embodiments of the present invention has been shown and described in detail with regard to only a few exemplary embodiments of the invention, it should be understood by those skilled in the art that it is not intended to limit the invention to the specific embodiments disclosed. Various modifications, omissions, and additions may be made to the disclosed embodiments without materially departing from the novel teachings and advantages of the invention, particularly in light of the foregoing teachings. Accordingly, it is intended to cover all such modifications, omissions, additions, and equivalents as may be included within the spirit and scope of the invention as defined by the following claims.

What is claimed is:

1. A suture to be used in a procedure applied to tissue, comprising: an elongated suture body including first and second ends; and a plurality of bi-directional retainers spaced apart from one another and extending from said elongated suture body between said first and second ends; wherein each bi-directional retainer is capable of initially being deployed through tissue in either one of a first or second direction, wherein said first and second directions are opposite one another, wherein: each bi-directional retainer can be collapsed in either of said first or second direction prior to deployment in tissue, the direction of collapse being dependent upon the direction in which the bi-directional retainer is deployed through tissue; once said bi-directional retainer is collapsed due to the bi-directional retainer being deployed through tissue in the first direction, the bi-directional retainer will yield to motion of the elongated suture body within the tissue when the elongated suture body is drawn in the first direction, and will resist motion of the elongated suture body in the second direction; and once said bi-directional retainer is collapsed due to the bi-directional retainer being deployed through tissue in the second direction, the bi-directional retainer will yield to motion of the elongated suture body within the tissue when the elongated suture body is drawn in the second direction, and will resist motion of the elongated suture body in the first direction, and wherein each bi-directional retainer includes grooves that guide how the bi-directional retainer collapses.

2. The suture of claim 1, wherein said bi-directional retainer collapses in said second direction when the bi-directional retainer is deployed through tissue in said first direction.

3. The suture of claim 1, wherein said grooves of each bi-directional retainer extend radially, from a location at which the bi-directional retainer is attached to said elongated suture body, to an outer edge of the bi-directional retainer.

4. The suture of claim 1, wherein each of said bi-directional retainers include vents to prevent air from getting trapped as said bi-directional retainers are deployed through tissue.

5. The suture of claim 1, wherein each of said bi-directional retainers, prior to being deployed through tissue, extend radially from and perpendicular to said elongated suture body.

6. The suture of claim 1, wherein said elongated suture body and said bi-directional retainers comprise a one piece structure.

7. The suture of claim 1, wherein: each of said bi-directional retainers includes an opening therethrough; said suture body is threaded through said openings of said bi-directional retainers; and said bi-directional retainers are attached to said suture body such that said bi-directional retainers are spaced apart from one another between said first and second ends of said elongated suture body.

8. The suture of claim 1, further comprising tissue engaging protrusions that extend from edges of said bi-directional retainers.

9. A suture to be used in a procedure applied to tissue, comprising: an elongated suture body including first and second ends; and a plurality of bi-directional retainers spaced apart from one another and extending from said elongated suture body between said first and second ends; wherein each bi-directional retainer is capable of initially being deployed through tissue in either one of a first or second direction, wherein said first and second directions are opposite one another, and once deployed in said tissue in said first direction, said retainer resists movement of the suture in the second direction, and once deployed in said tissue in said second direction, said retainer resists movement of the suture in the first direction, wherein each retainer includes grooves, perforations, or other fold lines along which the retainer can bend when the retainer is deployed through tissue, and wherein said grooves, perforations, or other fold lines of a said retainer extend radially, from a location at which the retainer is attached to said elongated suture body, to an outer edge of the retainer.

* * * * *